(12) United States Patent
Lubisch et al.

(10) Patent No.: US 6,562,827 B1
(45) Date of Patent: May 13, 2003

(54) HETEROCYCLICALLY SUBSTITUTED AMIDES USED AS CALPAIN INHIBITORS

(75) Inventors: Wilfried Lubisch, Heidelberg (DE); Achim Möller, Grünstadt (DE); Hans-Jörg Treiber, Brühl (DE); Monika Knopp, Ludwigshafen (DE)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/647,681

(22) PCT Filed: Apr. 20, 1999

(86) PCT No.: PCT/EP99/02632

§ 371 (c)(1),
(2), (4) Date: Oct. 3, 2000

(87) PCT Pub. No.: WO99/54305

PCT Pub. Date: Oct. 28, 1999

(30) Foreign Application Priority Data

Apr. 20, 1998 (DE) .......................... 198 17 462

(51) Int. Cl.[7] .................. A61K 31/55; A61K 31/495; C07D 223/00; C07D 241/00; C07D 401/00
(52) U.S. Cl. ................. 514/252.13; 514/211.01; 514/247; 514/253.01; 540/484; 540/524; 544/358; 544/360; 546/1; 546/268.1; 546/329; 546/339
(58) Field of Search .............. 514/211.01, 252.13, 514/253.01, 247; 544/360, 358; 540/484, 524; 546/1, 268.1, 329, 339

(56) References Cited

FOREIGN PATENT DOCUMENTS

| DE | 19642591 | 4/1998 |
|---|---|---|
| EP | 520 336 | 12/1992 |
| EP | 520336 | * 12/1992 |
| WO | 98/25883 | 6/1998 |
| WO | 98/41506 | 9/1998 |
| WO | 99/17775 | 4/1999 |

OTHER PUBLICATIONS

BASF OZ 0050/47592 (no ser. No.)=WO 98/25883.
BASF OZ 0050/47412 (no ser. No.)=DE 196 42591.

* cited by examiner

Primary Examiner—Richard L. Raymond
Assistant Examiner—Sudhaker B. Patel
(74) Attorney, Agent, or Firm—Wood, Phillips, Katz, Clark & Mortimer

(57) ABSTRACT

Heterocyclically substituted amides of the general formula I

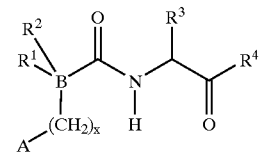

wherein the variables as defined in the specification are useful in pharmaceuticals for the treatment of diseases in which increased interleuken-1 levels occur.

23 Claims, No Drawings

HETEROCYCLICALLY SUBSTITUTED AMIDES USED AS CALPAIN INHIBITORS

The present invention relates to novel heterocyclically substituted amides, which are inhibitors of enzymes, in particular cysteine proteases, such as calpain (=calcium-dependent cysteine proteases) and its isoenzymes and cathepsins, for example B and L.

Calpains are intracellular, proteolytic enzymes from the so-called cysteine proteases group and are found in many cells. The enzyme calpain is activated by an increased calcium concentration, a differentiation being made between calpain I or µ-calpain, which is activated by µ-molar concentrations of calcium ions, and calpain II or m-calpain, which is activated by m-molar concentrations of calcium ions (P. Johnson, Int. J. Biochem. 1990, 22(8), 811–22). The existence of further calpain isoenzymes is postulated today (K. Suzuki et al., Biol. Chem. Hoppe-Seyler, 1995, 376(9), 523–9).

It is suspected that calpains play an important part in various physiological processes. These include cleavage of regulatory proteins such as protein kinase C, cytoskeletal proteins such as MAP 2 and spectrin, muscle proteins, protein breakdown in rheumatoid arthritis, proteins in the activation of platelets, neuropeptide metabolism, proteins in mitosis and others which are listed in M. J. Barrett et al., Life Sci. 1991, 48, 1659–69 and K. K. Wang et al., Trends in Pharmacol. Sci., 1994, 15, 412–9.

Increased calpain levels have been measured in various pathophysiological processes, for example: ischemia of the heart (e.g. cardiac infarct), of the kidney or of the central nervous system (e.g. "stroke"), inflammations, muscular dystrophies, cataracts of the eyes, injuries to the central nervous system (e.g. trauma), Alzheimer's disease etc. (see K. K. Wang, above). A relationship of these diseases with increased and lasting intracellular calcium levels is suspected. As a result, calcium-dependent processes are overactivated and are no longer subject to physiological regulation. Accordingly, overactivation of calpains can also initiate pathophysiological processes. It was therefore postulated that inhibitors of the calpain enzymes can be useful for the treatment of these diseases. Various investigations confirm this. Thus Seung-Chyul Hong et al., Stroke 1994, 25(3), 663–9 and R. T. Bartus et al., Neurological Res. 1995, 17, 249–58 have shown a neuroprotective action of calpain inhibitors in acute neurodegenerative disorders or ischemias, such as occur after cerebral stroke. Likewise, after experimental brain traumata, calpain inhibitors improved recovery from the memory power deficits and neuromotor disorders which occurred (K. E. Saatman et al. Proc. Natl. Acad. Sci. USA, 1996, 93, 3428–3433). C. L. Edelstein et al., Proc. Natl. Acad. Sci. USA, 1995, 92, 7662–6, found a protective action of calpain inhibitors on kidneys damaged by hypoxia. Yoshida, Ken Ischi et al., Jap. Circ. J. 1995, 59(1) 40–8, were able to show favorable effects of calpain inhibitors after cardiac damage which was produced by ischemia or reperfusion. Since calpain inhibitors inhibit the release of the β-AP4 protein, potential use as a therapeutic for Alzheimer's disease was proposed (J. Higaki et al., Neuron, 1995, 14, 651–59). The release of interleukin-1α was also inhibited by calpain inhibitors (N. Watanabe et al., Cytokine 1994, 6(6), 597–601). It was furthermore found that calpain inhibitors show cytotoxic effects on tumor cells (E. Shiba et al., 20th Meeting Int. Ass. Breast Cancer Res., Sendai Jp, Sep. 25–28, 1994, Int. J. Oncol. 5(Suppl.), 1994, 381).

Further possible uses of calpain inhibitors are listed in K. K. Wang, Trends in Pharmacol. Sci., 1994, 15, 412–8.

Calpain inhibitors have already been described in the literature. These are mainly, however, either irreversible or peptide inhibitors. As a rule, irreversible inhibitors are alkylating substances and have the disadvantage that they react non-selectively in the body or are unstable. Thus these inhibitors often show undesirable side effects, such as toxicity, and are accordingly restricted in their use or unutilizable. Among the irreversible inhibitors can be included, for example, the epoxides E 64 (E. B. McGowan et al., Biochem. Biophys. Res. Commun. 1989, 158, 432–5), α-haloketones (H. Angliker et al., J. Med. Chem. 1992, 35, 216–20) or disulfides (R. Matsueda et al., Chem. Lett. 1990, 191–194).

Many known reversible inhibitors of cysteine proteases, such as calpain, are peptide aldehydes, in particular dipeptide and tripeptide aldehydes such as, for example, Z-Val-Phe-H (MDL 28170) (S. Mehdi, Trends in Biol. Sci. 1991, 16, 150–3) and the compounds from EP 520336.

Peptide ketone derivatives have also been disclosed as inhibitors of cysteine proteases and in particular calpain. However, only ketones, in which, on the one hand, leaving groups in the α-position cause an irreversible inhibition and, on the other hand, a carboxylic acid derivative activates the keto group, were found to be effective inhibitors (see M. R. Angelastro et al., see above; WO 92/11850; WO 92,12140; WO 94/00095 and WO 95/00535). However, of these ketoamides and ketoesters, hitherto only peptide derivatives have been described as effective (Zhaozhao Li et al., J. Med. Chem. 1993, 36, 3472–80; S. L. Harbenson et al., J. Med. Chem. 1994, 37, 2918–29 and see above M. R. Angelastro et al.).

Until now, it has never been shown that nonpeptide ketones are also potent, reversible calpain inhibitors. The aim is thus to obtain nonpeptide inhibitors which are derived from carbonyl compounds and improve the general problems of peptides (metabolic stability, poor crossing of the cell membranes etc.).

Ketobenzamides are already known in the literature. Thus the ketoester PhCO—Abu—COOCH$_2$CH$_3$ was described in WO 91/09801, WO 94/00095 and 92/11850. The analogous phenyl derivative Ph—CONH—CH (CH$_2$Ph)—CO—COOCH$_3$ was found in M. R. Angelastro et al., J. Med. Chem. 1990, 33, 11–13 to be, however, only a weak calpain inhibitor. This derivative is also described in J. P. Burkhardt, Tetrahedron Lett., 1988, 3433–36. The significance of the heterocyclically substituted amides, however, has never been investigated until now.

On the other hand, there are attempts to find reversible nonpeptide calpain inhibitors. Thus in JP 8183759, JP 8183769, JP 8183771 and EP 520336 aldehydes derived from dipeptides have already been described, saturated carbocyclic rings, for example cyclohexanes, or saturated heterocyclic rings, for example piperidines, being incorporated into these peptide inhibitors instead of an amino acid and novel aldehydes being obtained as calpain inhibitors.

In the present invention, substituted nonpeptide heterocyclically substituted amide derivatives are described. These compounds are new and surprisingly have the possibility of obtaining potent nonpeptide inhibitors of cysteine proteases, such as, for example, calpain, by incorporation of rigid structural fragments.

The present invention relates to heterocyclically substituted amides of the general formula I

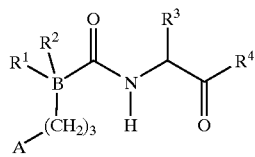

I and their tautomeric and isomeric forms, possible enantiomeric and diastereomeric forms, as well as possible physiologically tolerable salts, in which the variables have the following meanings:

A is piperazine, homopiperazine, piperidine or pyrrolidine, which can additionally carry a radical $R^5$ and B is a phenyl, pyridine, pyrimidine, pyrazine or pyridazine ring and $R^1$ and $R^2$ independently of one another are hydrogen, $C_1$–$C_6$-alkyl, which is branched or unbranched, O—$C_1$–$C_6$-alkyl, which is branched or unbranched, OH, Cl, F, Br, I, $CF_3$, $NO_2$, $NH_2$, CN, COOH, COO—$C_1$–$C_4$-alkyl, NHCO—$C_1$–$C_4$-alkyl, NHCO-phenyl, CONHR$^9$, NHSO$_2$—$C_1$–$C_4$-alkyl, NHSO$_2$-phenyl, SO$_2$—$C_1$–$C_4$-alkyl and SO$_2$-phenyl and $R^1$ and $R^2$ can be a chain —CH=CH—CH=CH—, which can additionally carry one or two substituents $R^6$, and $R^3$ is $C_1$–$C_6$-alkyl, which is branched or unbranched and which can additionally carry an S—$CH_3$ radical, cyclohexyl, cyclopentyl, cycloheptyl, phenyl, pyridyl, pyrimidyl, pyridazyl, pyrazyl, indolyl, thienyl or naphthyl ring, where the rings are substituted by at most two radicals $R^7$, and $R^7$ is hydrogen, $C_1$–$C_4$-alkyl, which is branched or unbranched, O—$C_1$–$C_4$-alkyl, OH, Cl, F, Br, I, $CF_3$, $NO_2$, $NH_2$, CN, COOH, COO—$C_1$–$C_4$-alkyl, CONHR$^9$, NHCO—$C_1$–$C_4$-alkyl, NHCO-phenyl, NHSO$_2$—$C_1$–$C_4$-alkyl, NHSO$_2$-phenyl, SO$_2$—$C_1$–$C_4$-alkyl and SO$_2$-phenyl, and $R^4$ is hydrogen, —COR$^8$, where $R^8$ can be —OR$^9$ and —NR$^9$R$^{10}$ and $R^5$ is hydrogen, $C_1$–$C_6$-alkyl, which is branched or unbranched, which can additionally carry a substituent $R^{11}$, or $R^5$ can be a phenyl, pyridyl, pyrimidyl, pyridazyl, pyrazinyl, pyrazolyl, naphtyl, thienyl, piperidinyl, pyrrolidinyl or imidazolyl ring, which can additionally carry one or two substituents $R^6$ and $R^6$ is hydrogen, $C_1$–$C_6$-alkyl, which is branched or unbranched, O—$C_1$–$C_6$-alkyl, which is branched or unbranched, OH, Cl, F, Br, I, $CF_3$, $NO_2$, $NH_2$, CN, COOH, COO—$C_1$–$C_4$-alkyl or $C_1$–$C_4$-alkyl-NR$^9$R$^{13}$ or two radicals $R^6$ can be a bridge OC(R$^9$)$_2$O and $R^9$ is hydrogen, $C_1$–$C_6$-alkyl, which is branched or unbranched, and $R^{10}$ is hydrogen, $C_1$–$C_6$-alkyl, which is branched or unbranched, which can additionally be substituted by a phenyl ring which can additionally carry a radical $R^{12}$, and by

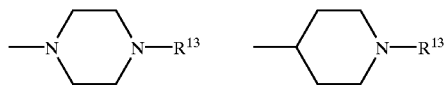

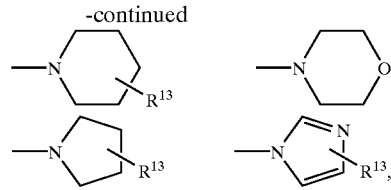

and $R^{11}$ can be a phenyl, pyridyl, pyrimidyl, naphtyl, thienyl, furyl, pyridazyl, pyrazinyl, pyrazolyl, pyrrolyl or imidazolyl ring which can additionally carry one or two substituents $R^6$, and $R^{12}$ is hydrogen, $C_1$–$C_6$-alkyl, which is branched or unbranched, O—$C_1$–$C_6$-alkyl, which is branched or unbranched, OH, Cl, F, Br, I, $CF_3$, $NO_2$, $NH_2$, CN, COOH, COO—$C_1$–$C_4$-alkyl and $R^{13}$ is hydrogen, a $C_1$–$C_4$-alkyl chain and $C_0$–$C_4$-alkylphenyl, where the phenyl ring can additionally carry one or two radicals $R^{12}$ and x is 0, 1 or 2.

The compounds of the formula I can be employed as racemates or as enantiomerically pure compounds or as diastereomers. If enantiomerically pure compounds are desired, these can be obtained, for example, by carrying out a classical racemate resolution with the compounds of the formula I or their intermediates using a suitable optically active base or acid. On the other hand, the enantiomeric compounds can likewise be prepared by use of commercially available compounds, for example optically active amino acids such as phenylalanine, tryptophan and tyrosine.

The present invention also relates to compounds which are mesomeric or tautomeric with compounds of the formula I, for example those in which the keto group of the formula I is present as an enol tautomer.

The invention also includes the acid addition salts of the compounds of the formula I with physiologically tolerable acids. Suitable physiologically tolerable organic and inorganic acids are, for example, hydrochloric acid, hydrobromic acid, phosphoric acid, sulfuric acid, oxalic acid, maleic acid, fumaric acid, lactic acid, tartaric acid, adipic acid and benzoic acid. Further utilizable acids are described in Fortschritte der Arzneimittelforschung, Volume 10, pages 224 ff., Birkhäuser Verlag, Basle and Stuttgart, 1966.

The amides according to the invention can be prepared in various ways, which have been outlined in the synthesis schemes 1, 2, 3 and 4.

The carboxylic acid esters III are obtained by reaction of the carboxylic acid esters II, where X is a leaving group such as chloride, bromide, iodide or tosylate, with the corresponding piperazine or piperidine derivatives. This reaction is carried out under customary conditions from the sodium or potassium amide of the secondary amines in solvents such as THF, DMF, toluene or benzene or in the presence of a Cu catalyst (see C. R. Larock, Comprehensive Organic Transformations, VCH Publisher, 1989, p. 397). In the examples in which B is a nitrogen-containing aromatic, the reaction is preferably carried out at elevated temperature in solvents such as DMF or THF, if appropriate in the presence of a base such as triethylamine, NaH or potassium carbonate and a crown ether. In the examples in which B is a phenyl ring and A a piperidine derivative and the A—B bond is established under C—C bond linkage, Suzuki couplings (Suzuki et al., THL 1986, 27, 6369) or couplings with tin organyls are carried out (see C. R. Larock, Comprehensive Organic Transformations, VCH Publisher, 1989, p. 64).

The carboxylic acid esters III are converted into the acids IV using acids or bases such as lithium hydroxide, sodium hydroxide or potassium hydroxide in aqueous medium or in mixtures of water and organic solvents such as alcohols or tetrahydrofuran at room temperature or elevated temperatures, such as 25–100° C. Acids IV are linked to an α-amino acid derivative, customary conditions being used, which are listed, for example, in Houben-Weyl, Methoden der organischen Chemie [Methods of Organic Chemistry], 4th Edition, E5, Chap. V, and C. R. Larock, Comprehensive Organic Transformations, VCH Publisher, 1989, Ch. 9.

The carboxylic acids IV are converted into "activated" acid derivatives R'—COOL, where L is a leaving group such as Cl, imidazole or N-hydroxybenzotriazole, and are then converted into the derivative V by reaction with an amino acid derivative $H_2N$—$CH(R^3)$—COOR. This reaction is carried out in anhydrous, inert solvents such as methylene chloride, tetrahydrofuran and dimethylformamide at temperatures from −20 to +25° C.

The derivatives V are converted into the ketocarboxylic acids VI analogously to the hydrolysis described above. The ketoesters I' are prepared in a reaction analogous to that of Dakin-West, the reaction being carried out according to a method of Zhaozhao Li et al., J. Med. Chem., 1993, 36, 3472–80. In this process, carboxylic acids such as VI are reacted with oxalic acid monoester chloride at elevated temperature (50–100° C.) in solvents, such as, for example, tetrahydrofuran, and the product thus obtained is then reacted with bases such as sodium ethoxide in ethanol at temperatures of 25–80° C. to give the ketoester I' according to the invention. The ketoesters I' can be hydrolyzed as described above, for example to ketocarboxylic acids according to the invention.

Synthesis Scheme 1

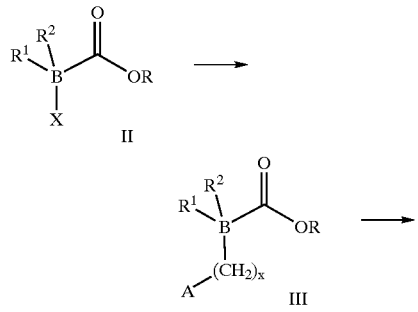

The reaction to give ketoamides I' is also carried out analogously to the method of Zhaozhao Li et al. (see above). The keto group in I' is protected by addition of 1,2-ethanedithiol under Lewis acid catalysis, such as, for example, boron trifluoride etherate, in inert solvents, such as methylene chloride, at room temperature, a dithiane being obtained. These derivatives are reacted with amines $R^8$—H in polar solvents, such as alcohols, at temperatures of 0–80° C., the ketoamides I ($R^8$=$NR^9R^{10}$) being obtained.

Synthesis Scheme 2

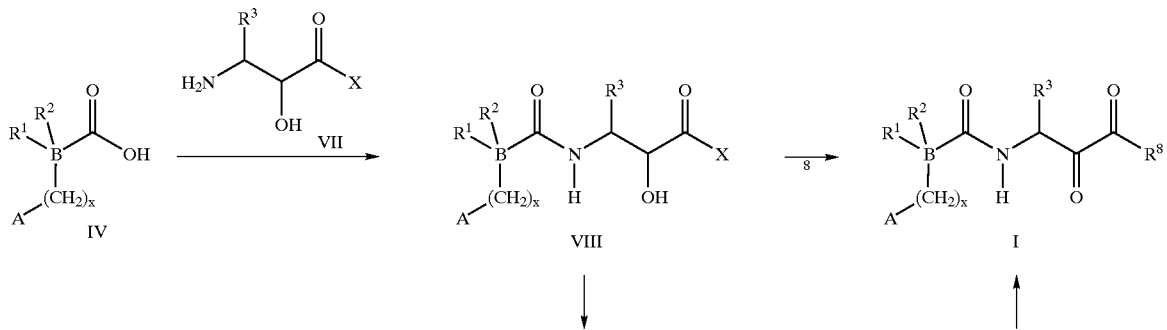

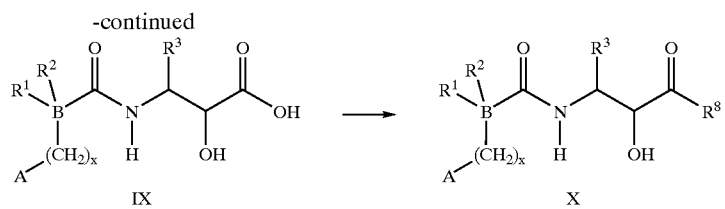

An alternative method is shown in scheme 2. The carboxylic acids IV are reacted with aminohydroxycarboxylic acid derivatives VII (for preparation of IV see S. L. Harbenson et al., J. Med. Chem. 1994, 37, 2918–29) under customary peptide coupling methods (see above, Houben-Weyl), amides VIII being obtained. These alcohol derivatives VIII can be oxidized to the ketocarboxylic acid derivatives I according to the invention. Use can be made for this of various customary oxidation reactions (see C. R. Larock, Comprehensive Organic Transformations, VCH Publisher, 1989, page 604 f.) such as, for example, Swern and Swern-analogous oxidations, preferably dimethyl sulfoxide/pyridine-sulfur trioxide complex in solvents such as methylene chloride or tetrahydrofuran, if appropriate with addition of dimethyl sulfoxide, at room temperature or temperatures of −50 to 25° C. (T. T. Tidwell, Synthesis 1990, 857–70) or sodium hypochloride/TEMPO (S. L. Harbenson et al., see above).

If VIII are α-hydroxy esters (X=O-alkyl), these can be hydrolyzed to carboxylic acids IX, the reaction being carried out analogously to the above methods, but preferably using lithium hydroxide in water/tetrahydrofuran mixtures at room temperature. The preparation of other esters or amides X is carried out by reaction with alcohols or amines under coupling conditions which have already been described. The alcohol derivative X can be oxidized again to give ketocarboxylic acid derivatives I according to the invention.

The aldehydes of the formula I according to the invention ($R^5$=hydrogen) can be prepared analogously to Synthesis Scheme 3.

Carboxylic acid derivatives IV are linked to suitable aminoalcohols XI to give the corresponding amides XII. Use is made here of customary peptide coupling methods, which are mentioned either in C. R. Larock, Comprehensive Organic Transformations, VCH Publisher, 1989, page 972f. or in Houben-Weyl, Methoden der organischen Chemie [Methods of Organic Chemistry], 4th Edition, E5, Chap. V. The reaction is preferably carried out using "activated" acid derivatives of III, the acid group COOH being converted into a group COL. L is a leaving group such as, for example, Cl, imidazole or N-hydroxybenzotriazole. This activated acid is then converted to the amides XII using amines. The reaction is carried out in anhydrous, inert solvents such as methylene chloride, tetrahydrofuran and dimethylformamide at temperatures from −20 to +25° C.

These alcohol derivatives XII can be oxidized to the aldehyde derivatives I according to the invention. It is possible to use various customary oxidation reactions for this (see C. R. Larock, Comprehensive Organic Transformations, VCH Publisher, 1989, page 604 f.) such as, for example, Swern and Swern-analogous oxidations (T. T. Tidwell, Synthesis 1990, 857–70), sodium hypochloride/TEMPO (S. L. Harbenson et al., see above) or Dess-Martin (J. Org. Chem. 1983, 48, 4155). Preferably, here the reaction is carried out in inert aprotic solvents such as dimethylformamide, tetrahydrofuran or methylene chloride using oxidants such as DMSO/pyridine×$SO_3$ or DMSO/oxalyl chloride at temperatures from −50 to +25° C., depending on the method (see above references).

Synthesis Scheme 3

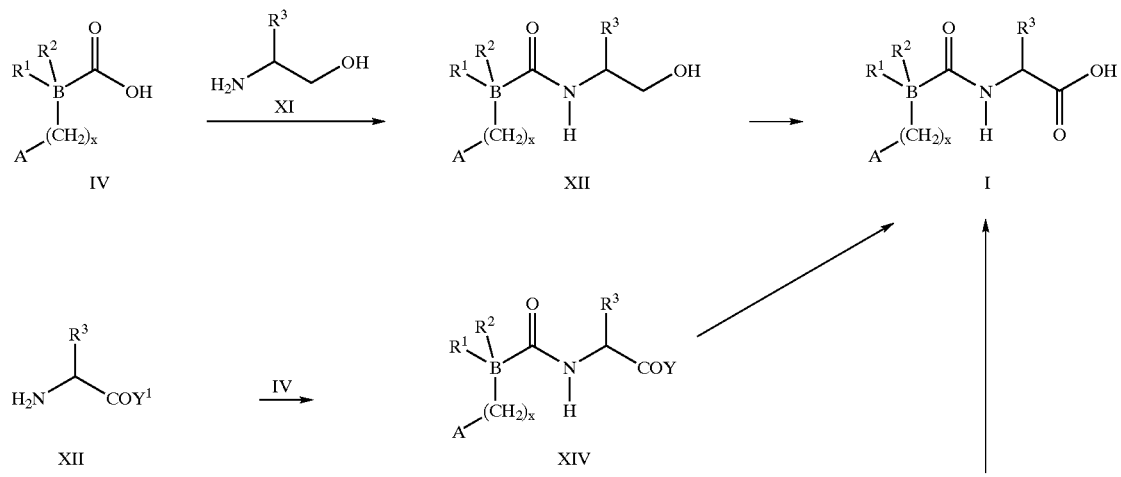

-continued

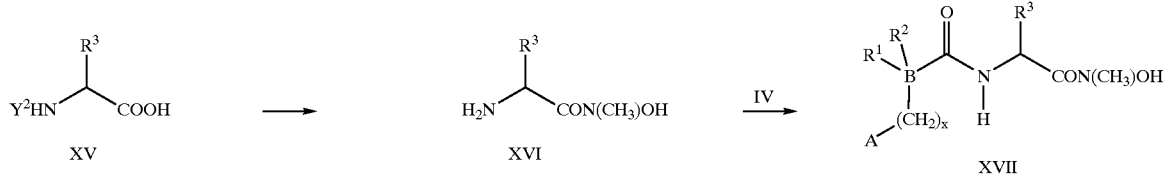

Alternatively, carboxylic acids IV can also be reacted with the esters or amides XIII. The resulting amides XIV can be converted into the aldehydes I according to the invention by reduction. These processes are listed in R. C. Larock, Comprehensive organic Transformations, VCH Publisher, 1989, page 619–26.

Analogously to the last process, benzoic acid IV can be reacted with the aminohydroxamic acid derivatives XVI to give the amides XVII. In this case use is made of the same reaction procedure as in the preparation of XII. The hydroxamic acid derivatives XVI are also obtainable from the protected amino acids XV by reaction with hydroxylamine. In this process, use is also made here of the amide preparation process which has already been described. The removal of the protective group $Y^2$, for example Boc, is carried out customarily, for example using trifluoroacetic acid in methylene chloride. The benzamidohydroxamic acids XVII thus obtained can be converted into the aldehydes I according to the invention by reduction. In this process, use is made, for example, of lithium aluminum hydride as a reductant at temperatures from –60 to 0° C. in inert solvents such as tetrahydrofuran or ether.

Synthesis Scheme 4

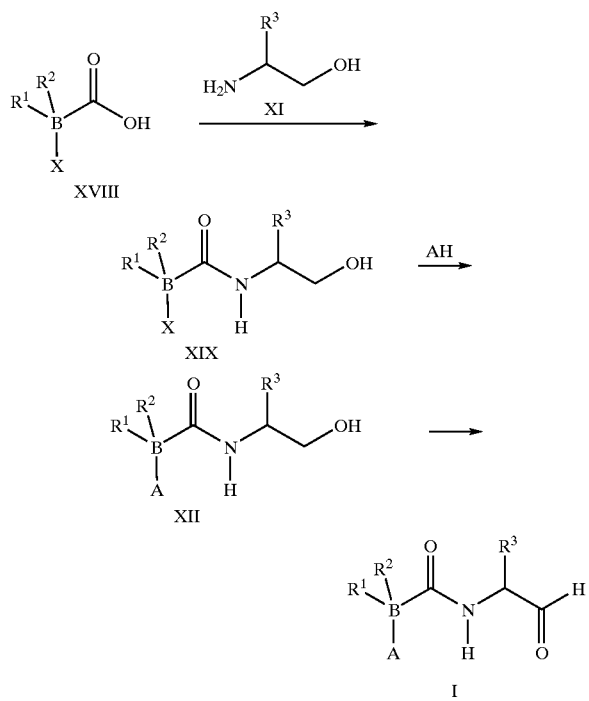

A further alternative which is suitable for the examples in which A is a piperazine derivative and B a pyridine derivative is described in scheme 4. The individual synthesis steps of this very short route have already been explained in detail in the previous remarks.

The ketobenzamides I contained in the present invention are inhibitors of cysteine proteases, in particular cysteine proteases such as the calpains I and II and cathepsins B and L. The inhibitory action of the ketobenzamides I was determined using enzyme tests customary in the literature, a concentration of the inhibitor at which 50% of the enzyme activity is inhibited (=$IC_{50}$) being determined as a scale of action. In some cases a $K_i$ value was also determined. The benzamides I were measured in this manner for inhibitory action of calpain I, calpain II and cathepsin B.

Cathepsin B Test

The cathepsin B inhibition was determined analogously to a method of S. Hasnain et al., J. Biol. Chem. 1993, 268, 235–40.

2 μL of an inhibitor solution, prepared from inhibitor and DMSO (final concentrations: 100 μM to 0.01 μM) are added to 88 μL of cathepsin B (cathepsin B from human liver (Calbiochem), diluted to 5 units in 500 μM buffer). This mixture is preincubated at room temperature (25° C.) for 60 minutes and the reaction is then started by addition of 10 μL of of 10 mM Z-Arg-Arg-pNA (in buffer with 10% DMSO). The reaction is monitored at 405 nM in a microtiter plate reader for 30 minutes. The $IC_{50}$s are then determined from the maximum gradients.

Calpain I and II Test

The testing of the inhibitory properties of calpain inhibitors is carried out in buffer using 50 mM tris HCl, pH 7.5; 0.1 M NaCl; 1 mM dithiotreithol; 0.11 mM $CaCl_2$, the fluorogenic calpain substrate Suc-Leu-Tyr-AMC (25 mM dissolved in DMSO, Bachem/Switzerland) being used. Human μ-calpain is isolated from erythrocytes and, after several chromatographic steps (DEAE-Sepharose, phenyl-Sepharose, Superdex 200 and Blue Sepharose), enzyme having a purity of >95%, assessed according to SDS-PAGE, Western blot analysis and N-terminal sequencing, is obtained. The fluorescence of the cleavage product 7-amino-4-methylcoumarin (AMC) is monitored in a Spex-Fluorolog fluorimeter at $\lambda_{ex}$=380 nm and $\lambda_{em}$=460 nm. In a measuring range of 60 min, the cleavage of the substrate is linear and the autocatalytic activity of calpain is low if the experiments are carried out at temperatures of 12° C. The inhibitors and the calpain substrate are added to the experimental batch as DMSO solutions, where DMSO should not exceed 2% in the final concentration.

In an experimental batch, 10 μl of substrate (250 μM final) and then 10 μl of μ-calpain (2 μg/ml final, i.e. 18 nM) are added to a 1 ml cuvette which contains buffer. The calpain-mediated cleavage of the substrate is measured for 15–20 min. 10 μl of inhibitor (50–100 μM solution in DMSO) are then added and the inhibition of the cleavage is measured for a further 40 min.

$K_i$ values are determined according to the classical equation for reversible inhibition:

$$K_i = I/(v_o/v_i) - 1$$

where

I=inhibitor concentration, $v_o$=initial velocity before addition of the inhibitor;

$v_i$=reaction velocity in equilibrium.

The velocity is calculated from v=release of AMC/time i.e. height/time.

Calpain is an intracellular cysteine protease. Calpain inhibitors must pass through the cell membrane in order to prevent the breakdown of intracellular proteins by calpain. Some known calpain inhibitors, such as, for example, E 64 and leupeptin, only cross the cell membranes with difficulty and accordingly show, although they are good calpain inhibitors, only a poor action in cells. The aim is to find compounds having better membrane accessibility. As a demonstration of the membrane accessibility of calpain inhibitors, we use human platelets.

Calpain-mediated Breakdown of Tyrosine Kinase pp60src in Platelets

After the activation of platelets, the tyrosine kinase pp60src is cleaved by calpain. This was investigated in detail by Oda et al. in J. Biol. Chem., 1993, Vol 268, 12603–12608. It was shown in this context that the cleavage of pp60src can be prevented by calpeptin, an inhibitor of calpain. The cellular effectiveness of our substances was tested following this publication. Fresh human blood treated with citrate was centrifuged at 200 g for 15 min. The platelet-rich plasma was pooled and diluted 1:1 with platelet buffer (platelet buffer: 68 mM NaCl, 2.7 mM KCl, 0.5 mM $MgCl_2 \times 6\ H_2O$, 0.24 mM $NaH_2PO_4 \times H_2O$, 12 mM $NaHCO_3$, 5.6 mM glucose, 1 mM EDTA, pH 7.4). After a centrifugation and washing step with platelet buffer, the platelets were adjusted to $10^7$ cells/ml. The isolation of the human platelets was carried out at RT.

In the test batch, isolated platelets ($2 \times 10^6$) were preincubated at 37° C. with different concentrations of inhibitors (dissolved in DMSO) for 5 min. The platelets were then activated with 1 μM ionophore A23187 and 5 mM $CaCl_2$. After incubation for 5 min, the platelets were briefly centrifuged at 13000 rpm and the pellet was taken up in SDS sample buffer (SDS sample buffer: 20 mM tris-HCl, 5 mM EDTA, 5 mM EGTA, 1 mM DTT, 0.5 mM PMSF, 5 μg/ml leupeptin, 10 μg/ml pepstatin, 10% glycerol and 1% SDS). The proteins were separated in a 12% strength gel and pp60src and its 52 kDa and 47 kDa cleavage products were identified by Western blotting. The polyclonal rabbit antibody anti-Cys-src (pp60$^{c-src}$) used was purchased from the company Biomol Feinchemikalien (Hamburg). This primary antibody was detected using an HRP-coupled second antibody from goats (Boehringer Mannheim, FRG). The Western blotting was carried out according to known methods.

The quantification of the cleavage of pp60src was carried out by densitometry, the controls used being nonactivated platelets (control 1: no cleavage) and platelets treated with ionophore and calcium (control 2: corresponds to 100% cleavage). The $ED_{50}$ value corresponds to the concentration of inhibitor at which the intensity of the color reaction is reduced by 50%.

Glutamate-induced Cell Death in Cortical Neurons

The test was carried out as in Choi D. W., Maulucci-Gedde M. A. and Kriegstein A. R., "Glutamate neurotoxicity in cortical cell culture". J. Neurosci. 1989, 7, 357–368.

The halves of the cortex were dissected from 15 day-old mouse embryos and the individual cells were obtained enzymatically (trypsin). These cells (glia and cortical neurons) are inoculated into 24-well plates. After three days (laminin-coated plates) or seven days (ornithine-coated plates), the mitosis treatment is carried out using FDU (5-fluoro-2-deoxyuridines). 15 days after the cell preparation, cell death is induced by addition of glutamate (15 minutes). After the removal of glutamate, the calpain inhibitors are added. 24 hours later, the cell damage is determined by means of the determination of lactate dehydrogenase (LDH) in the cell culture supernatant.

It is postulated that calpain also plays a part in apoptotic cell death (M. K. T. Squier et al. J. Cell. Physiol. 1994, 159, 229–237; T. Patel et al. Faseb Journal 1996, 590, 587–597). Therefore, in a further model, cell death was induced with calcium in the presence of a calcium ionophore in a human cell line. Calpain inhibitors must pass into the cell and inhibit calpain there in order to prevent the induced cell death.

Calcium-mediated Cell Death in NT2 Cells

Cell death can be induced in the human cell line NT2 (Stratagene GmbH) by means of calcium in the presence of the ionophore A 23187. $10^5$ cells/well were plated out into microtiter plates 20 hours before the experiment. After this period, the cells were incubated with various concentrations of inhibitors in the presence of 2.5 μM ionophore and 5 mM calcium. 0.05 ml of XTT (cell proliferation kit II, Boehringer Mannheim) was added to the reaction batch after 5 hours. The optical density is determined approximately 17 hours later, according to the instructions of the manufacturer, in the Easy Reader EAR 400 from the company SLT. The optical density at which half of the cells have died is calculated from the two controls with cells without inhibitors, which were incubated in the absence and presence of ionophore.

In a number of neurological diseases or psychological disorders, increased glutamate activity, which leads to states of overstimulation or toxic effects in the central nervous system (CNS), occurs. Glutamate mediates its effects by means of various receptors. Two of these receptors are classified by the specific agonists as NMDA receptor and AMPA receptor. Substances which weaken these glutamate-mediated effects can thus be employed for the treatment of these diseases, in particular for therapeutic administration against neurodegenerative diseases such as Huntington's disease and Parkinson's disease, neurotoxic disorders after hypoxia, anoxia, ischemia and after lesions, such as occur after stroke and trauma, or alternatively as antiepileptics (cf. Arzneim. Forschung 1990, 40, 511–514; TIPS, 1990, 11, 334–338; Drugs of the Future 1989, 14, 1059–1071).

Protection Against Cerebral Overstimulation by Excitatory Amino Acids (NMDA or AMPA Antagonism in Mice)

As a result of intracerebral administration of excitatory amino acids (EAA), such a massive overstimulation is induced that in a short time this leads to spasms and to the death of the animals (mice). These symptoms can be inhibited by systemic, e.g. intraperitoneal, administration of centrally active active compounds (EAA antagonists). Since the excessive activation of EAA receptors of the central nervous system plays an important part in the pathogenesis of various neurological disorders, a conclusion can be drawn from the demonstrated EAA antagonism in vivo on a possible therapeutic utility of the substances against CNS disorders of this type. As a measure of the efficacy of the substances, an $ED_{50}$ value was determined at which 50% of the animals are symptom-free as a result of a fixed dose of either NMDA or AMPA as a result of the prior i.p. administration of the standard substance.

It has already been shown that calpain inhibitors also show protective action against the cell death induced by EAA in cell cultures (H. Cauer et al., Brain Research 1993, 607, 354–356; Yu Cheg and A. Y. Sun, Neurochem. Res. 1994, 19, 1557–1564). The calpain inhibitors contained in this application are surprisingly active even against the spasms induced in vivo (mouse) by EAA (e.g. NMDA or AMPA) and thus indicate a possible therapeutic use in the abovementioned CNS disorders.

The heterocyclically substituted amides I are inhibitors of cysteine derivatives such as calpain I or II and cathepsin B or L and can thus be used for the control of diseases which are associated with an increased enzyme activity of the calpain enzymes or cathepsin enzymes. The present amides I can accordingly be used for the treatment of neurodegenerative processes which occur after ischemia, trauma, subarachnoid hemorrhages and stroke, and of neurodegenerative diseases such as multiple infarct dementia, Alzheimer's disease, Huntington's disease and of epilepsies and furthermore for the treatment of damage to the heart after cardiac ischemia, damage and reperfusion after vascular occlusion, damage to the kidneys after renal ischemia, skeletal muscle damage, muscular dystrophy, damage which occurs due to proliferation of the smooth muscle cells, coronary vasospasms, cerebral vasospasms, cataracts of the eyes, restenosis of the bloodstreams after angioplasty. Moreover, the amides I can be useful in the chemotherapy of tumors and metastasis thereof and for the treatment of diseases in which an increased interleukin-1 level occurs, such as in inflammations and rheumatic disorders.

In addition to the customary pharmaceutical auxiliaries, the pharmaceutical preparations according to the invention contain a therapeutically efficacious amount of the compounds I.

For local external application, for example in powders, ointments or sprays, the active compounds can be contained in the customary concentrations. As a rule, the active compounds are contained in an amount from 0.001 to 1% by weight, preferably 0.001 to 0.1% by weight.

In the case of internal administration, the preparations are administered in individual doses. 0.1 to 100 mg are provided in an individual dose per kg of body weight. The preparation can be administered daily in one or more doses depending on the nature and severity of the disorders.

According to the desired type of administration, the pharmaceutical preparations according to the invention contain the customary excipients and diluents in addition to the active compound. For local external application, pharmaceutical auxiliaries such as ethanol, isopropanol, ethoxylated castor oil, ethoxylated hydrogenated castor oil, polyacrylic acid, polyethylene glycol, polyethylene glycol stearate, ethoxylated fatty alcohols, paraffin oil, petroleum jelly and wool fat can be used. For internal administration, for example, lactose, propylene glycol, ethanol, starch, talc and polyvinylpyrrolidone are suitable.

Antioxidants such as tocopherol and butylated hydroxyanisole as well as butylated hydroxytoluene, flavor-enhancing additives, stabilizers, emulsifiers and lubricants can additionally be contained.

The substances contained in the preparation in addition to the active compound and the substances used in the production of the pharmaceutical preparations are toxicologically acceptable and compatible with the respective active compound. The pharmaceutical preparations are produced in a customary manner, for example by mixing the active compound with other customary excipients and diluents.

The pharmaceutical preparations can be administered in various administration procedures, for example, orally, parenterally such as intravenously by infusion, subcutaneously, intraperitoneally and topically. Thus preparation forms such as tablets, emulsions, infusion and injection solutions, pastes, ointments, gels, creams, lotions, powders and sprays are possible.

EXAMPLES

Example 1

2-(4-(Pyrid-4-yl)piperazin-1-yl)nicotinic Acid N-(3-Phenylpropan-1-al-2-yl)amide a) Methyl 2-(4-(Pyrid-4-yl)piperazin-1-yl)nicotinate 3.4 g of methyl chloronicotinate, 5.5 g of potassium carbonate, 3.3 g of 4-pyridylpiperazine and a spatula tipful of 18-crown-6 were heated at 100° C. for 5 h in 75 ml of DMF and then stirred at room temperature for 60 h. The excess potassium carbonate was filtered off, the filtrate was concentrated and the residue was partitioned between water and ethyl acetate. After drying the organic phase over magnesium sulfate and concentrating the solvent, 3.9 g (82%) of the product were obtained.

b) 2-(4-(Pyrid-4-yl)piperazin-1-yl)nicotinic Acid 5.6 g of the intermediate compound Ia were introduced into 100 ml of THF and treated at room temperature with 1.4 g of LiOH in 50 ml of water. The cloudy solution was clarified by addition of 10 ml of MeOH. The reaction mixture was stirred at room temperature for 12 h and hydrolyzed using an equimolar amount of 1 M HCl. The reaction mixture was concentrated to dryness and the residue was taken up in methanol/toluene. After removing the solvent, 8.2 g of the still salt-containing product were obtained, which were employed in the next stage without further purification.

c) 2-(4-(Pyrid-4-yl)piperazin-1-yl)nicotinic Acid N-(3-Phenylpropan-1-ol-2-yl)amide 8.2 g of the intermediate compound 1b and 5.2 g of triethylamine were introduced into 200 ml of methylene chloride and 50 ml of DMF. 5 g of sodium sulfate were added and the mixture was stirred for 30 min. 2.6 g of phenylalaninol, 2.3 g of HOBT and 3.6 g of EDC were added successively at 0° C. and the mixture was stirred overnight at room temperature. The reaction mixture was poured onto distilled water, rendered alkaline with $NaHCO_3$, saturated with NaCl and extracted three times with 100 ml of methylene chloride. The organic phases were washed twice with water and dried over magnesium sulfate. After concentrating the solvent, 0.61 g (8%) of the product was obtained.

d) 2-(4-(Pyrid-4-yl)piperazin-1-yl)nicotinic Acid N-(3-Phenylpropan-1-al-2-yl)amide 0.6 g of the intermediate compound 1c were introduced into 20 ml of DMSO in the presence of 0.6 g of triethylamine and the mixture was treated with 0.9 g of $SO_3$-pyridine complex. It was stirred at room temperature overnight. The batch was poured onto 250 ml of distilled water, rendered alkaline with $NaHCO_3$, saturated with NaCl, extracted with 100 ml of methylene chloride and dried over magnesium sulfate. After concentrating the solvent, the residue was dissolved in THF and the hydrochloride was precipitated with HCl in dioxane. The product was filtered off with suction and washed several times with ether.

Yield: 0.08 g (11%); MS: m/e=488 ($M^+$).

Example 2

2-(4-Methylpiperazin-1-yl)nicotinic Acid N-(3-Phenylpropan-1-al-2-yl)amide a) Methyl 2-(4-Methylpiperazin-1-yl)nicotinate 3.4 g of methyl chloronicotinate, 5.5 g of potassium carbonate and 2.0 g of N-methylpiperazine were reacted in 50 ml of DMF analogously to Example 1a, 3.9 g (82%) of the product being obtained.

b) 2-(4-Methylpiperazin-1-yl)nicotinic Acid 3.5 g of the intermediate compound 2a in 100 ml of THF were reacted at room temperature with 1.1 g of LiOH in 50 ml of water and 10 ml of MeOH analogously to Example 1b, 6.1 g of the still salt-containing product being obtained, which were employed in the next stage without further purification.

c) 2-(4-Methylpiperazin-1-yl)nicotinic Acid N-(3-Phenylpropan-1-ol-2-yl)amide 6.1 g of intermediate compound 2b were reacted with 2.1 g of phenylalaninol in 100 ml of DMF in the presence of 2.7 g of EDC, 1.9 g of HOBT and 5.0 g of triethylamine analogously to Example 1c, 1.2 g (23%) of the product being obtained.

d) 2-(4-Methylpiperazin-1-yl)nicotinic Acid N-(3-Phenylpropan-1-al-2-yl)amide 1.0 g of the intermediate compound 2c were oxidized using 1.9 g of $SO_3$-pyridine complex in 25 ml of DMSO in the presence of 1.2 ml of triethylamine analogously to Example 1d, 0.7 g (60%) of the product being obtained in the form of the hydrochloride.

$^1$H NMR ($d_6$-DMSO): δ=2.5 (3H), 2.7–3.9 (10H), 4.7 (1H), 6.9–7.9 (6H), 8.1–8.2 (2H), 9.7 (1H), 10.9 (1H) ppm.

Example 3

2-(4-(Pyrimid-2-yl)piperazin-1-yl)nicotinic Acid N-(3-Phenylpropan-1-al-2-yl)amide a) Methyl 2-(4-(Pyrimid-2-yl)piperazin-1-yl)nicotinate 3.4 g of methyl chloronicotinate, 11.1 g of potassium carbonate and 4.7 g of N-(2-pyrimidyl)piperazine dihydrochloride were reacted in 75 ml of DMF analogously to Example 1a, 4.6 g (78%) of the product being obtained.

b) 2-(4-(Pyrimid-2-yl)piperazin-1-yl)nicotinic Acid 4.3 g of the intermediate compound 3a in 100 ml of THF were reacted at room temperature with 1.0 g of LiOH in 50 ml of water and 10 ml of MeOH analogously to Example 1b, 6.1 g of the still salt-containing product being obtained, which were employed in the next stage without further purification.

c) 2-(4-(Pyrimid-2-yl)piperazin-1-yl)nicotinic Acid N-(3-Phenylpropan-1-ol-2-yl)amide 3.8 g of intermediate compound 3b were introduced into 200 ml of methylene chloride and 50 ml of DMF in the presence of 4.0 g of triethylamine and 5 g of sodium sulfate analogously to Example 1c and treated successively with 2.0 g of phenylalaninol, 2.7 g of EDC and 1.8 g of HOBT, 1.5 g (28%) of the product being obtained.

d) 2-(4-(Pyrimid-2-yl)piperazin-1-yl)nicotinic Acid N-(3-Phenylpropan-1-al-2-yl)amide 1.3 g of the intermediate compound 3c were oxidized using 1.9 g of $SO_3$-pyridine complex in 20 ml of DMSO in the presence of 1.2 ml of triethylamine analogously to Example 1d, 0.7 g (48%) of the product being obtained in the form of the hydrochloride.

$^1$H NMR ($d_6$-DMSO): δ=2.9 (1H), 3.2–3.9 (9H), 4.8 (1H), 6.7 (1H), 7.0–7.4 (5H), 7.8 (1H), 8.2 (1H), 8.3 (4H), 9.1 (1H), 9.6 (1H) ppm.

Example 4

2-(4-Benzylpiperazin-1-yl)nicotinic Acid N-(3-Phenylpropan-1-al-2-yl)amide a) Methyl 2-(4-Benzylpiperazin-1-yl)nicotinate 3.4 g of methyl 2-chloronicotinate, 5.5 g of potassium carbonate and 3.5 g of N-benzylpiperazine were reacted in 75 ml of DMF analogously to Example 1a, 6.2 g (100%) of the product being obtained.

b) 2-(4-Benzylpiperazin-1-yl)nicotinic Acid 6.2 g of the intermediate compound 4a in 100 ml of THF were hydrolyzed using 1.4 g of LiOH analogously to Example 1b, 8.70 g of the still salt-containing product being obtained, which were employed in the next stage without further purification.

c) 2-(4-Benzylpiperazin-1-yl)nicotinic Acid N-(3-Phenylpropan-1-ol-2-yl)amide 5.6 g of the intermediate compound 4b were introduced into 200 ml of methylene chloride and 50 ml of DMF in the presence of 5.7 g of triethylamine and 5 g of sodium sulfate analogously to Example 1c, and treated successively with 2.9 g of phenylalaninol, 2.6 g of HOBT and 4.0 g of EDC, 1.0 g (12%) of the product being obtained.

d) 2-(4-Benzylpiperazin-1-yl)nicotinic Acid N-(3-Phenylpropan-1-al-2-yl)amide 0.9 g of the intermediate compound 4c was oxidized using 1.2 g of $SO_3$-pyridine complex in 20 ml of DMSO in the presence of 0.8 g of triethylamine analogously to Example 1d, 0.7 g (72%) of the product being obtained in the form of the hydrochloride.

$^1$H NMR ($d_6$-DMSO): δ=2.8–3.5 (8H), 3.6 (1H), 3.8 (1H), 4.3 (2H), 4.7 (1H), 6.9–7.8 (12H), 8.3 (1H), 9.1 (1H), 9.7 (1H), 11.7 (2H) ppm.

Example 5

2-(4-(Picol-2-yl)piperazin-1-yl)nicotinic Acid N-(3-Phenylpropan-1-al-2-yl)amide a) Methyl 2-(4-(Picol-2-yl)piperazin-1-yl)nicotinate 2.6 g of methyl 2-chloronicotinate were reacted with 2.7 g of 2-picolylpiperazine in 50 ml of DMF in the presence of 4.2 g of potassium carbonate analogously to Example 1a, 1.7 g (36%) of the product being obtained.

b) 2-(4-(Picol-2-yl)piperazin-1-yl)nicotinic Acid 1.7 g of the intermediate compound 5a were heated to 80° C. with 20 ml of 2M NaOH for 1 h. As soon as all the starting material had dissolved, the reaction mixture was concentrated, the residue was treated with 15 ml of 4M HCl solution in dioxane and, after removing the dioxane, the residue was taken up in methanol, and the precipitate was filtered off. The filtrate was treated with methylene chloride, dried over sodium sulfate, filtered and concentrated, 2.9 g of the still salt-containing product being obtained, which were employed in the next stage without further purification.

c) 2-(4-(Picol-2-yl)piperazin-1-yl)nicotinic Acid N-(3-Phenylpropan-1-ol-2-yl)amide 3.0 g of the intermediate compound 5b were introduced into 50 ml of methylene chloride and 4 ml of DMF in the presence of 4.5 ml of triethylamine, treated successively with 0.8 g of phenylalaninol, 0.7 g of HOBT and 1.2 g of EDC and stirred at room temperature for 12 h. The reaction mixture was filtered through a thin silica gel layer, the filtrate was rendered alkaline using 2M NaOH and the organic phase was separated off. The organic phase was extracted with 1 N HCl solution, and the aqueous phase was neutralized with NaOH and extracted with methylene chloride. The combined organic phases were dried over magnesium sulfate, filtered off and concentrated, 1.3 g (56%) of the product being obtained.

d) 2-(4-(Picol-2-yl)piperazin-1-yl)nicotinic Acid N-(3-Phenylpropan-1-al-2-yl)amide 1.3 g of the intermediate compound 5c were oxidized using 2.6 g of $SO_3$-pyridine complex in 30 ml of methylene chloride and 4 ml of DMSO in the presence of 3.7 g of triethylamine analogously to Example 1d. The product was precipitated as the hydrochloride, 0.3 g (23%) of the product being obtained in the form of the hydrochloride.

$^1$H NMR ($d_6$-DMSO): δ=3.0–3.8 (10H), 4.5 (3H), 7.0–7.3 (4H), 7.4 (3H), 7.7 (2H), 8.0 (2H), 8.4 (1H), 8.7 (1H), 9.6 (1H) ppm.

Example 6

2-(4-(Picol-3-yl)piperazin-1-yl)nicotinic Acid N-(3-Phenylpropan-1-al-2-yl)amide a) Methyl 2-(4-(Picol-3-yl)piperazin-1-yl)nicotinate 2.6 g of methyl 2-chloronicotinate were reacted with 2.7 g of 3-picolylpiperazine in 50 ml of DMF in the presence of 4.2 g of potassium carbonate analogously to Example 1a, 1.2 g (25%) of the product being obtained.

b) 2-(4-(Picol-3-yl)piperazin-1-yl)nicotinic Acid 1.2 g of the intermediate compound 6a were hydrolyzed at 80° C. using 20 ml of 2M NaOH analogously to Example 5b, 2.2 g of the still salt-containing product being obtained, which were employed in the next stage without further purification.

c) 2-(4-(Picol-3-yl)piperazin-1-yl)nicotinic Acid N-(3-Phenylpropan-1-ol-2-yl)amide 2.2 g of the intermediate compound 6b were dissolved in 50 ml of methylene chloride and 4 ml of DMF in the presence of 4 ml of triethylamine analogously to Example 5c and treated successively with 0.6 g of phenylalaninol, 0.5 g of HOBT and 0.9 g of EDC, 1.7 g (42%) of the product being obtained.

d) 2-(4-(Picol-3-yl)piperazin-1-yl)nicotinic Acid N-(3-Phenylpropan-1-al-2-yl)amide 1.7 g of the intermediate compound 6c were oxidized using 4.1 g of $SO_3$-pyridine complex in 6 ml of DMSO and 30 ml of methylene chloride in the presence of 6.1 ml of triethylamine analogously to Example 1d. The product was precipitated as the hydrochloride, 0.6 g (32%) of the product being obtained.

$^1$H NMR ($d_6$-DMSO): δ=3.0–3.6 (10H), 4.5 (3H), 7.0–7.5 (7H), 8.0 (1H), 8.2 (1H), 8.4 (1H), 8.8 (1H), 9.0 (1H), 9.2 (1H), 9.6 (1H) ppm.

Example 7

2-(4-(Picol-4-yl)piperazin-1-yl)nicotinic Acid N-(3-Phenylpropan-1-al-2-yl)amide a) Methyl 2-(4-(Picol-4-yl)piperazin-1-yl)nicotinate 3.7 g of methyl 2-chloronicotinate were reacted with 2.5 g of 4-picol-4-ylpiperazine in 50 ml of DMF in the presence of 4.0 g of potassium carbonate analogously to Example 1a, 2.9 g (62%) of the product being obtained.

b) 2-(4-(Picol-4-yl)piperazin-1-yl)nicotinic Acid 2.9 g of the intermediate compound 7a were hydrolyzed at 60° C. using 20 ml of 2M NaOH analogously to Example 5b, 3.4 g of the still salt-containing product being obtained, which were employed in the next stage without further purification.

c) 2-(4-(Picol-4-yl)piperazin-1-yl)nicotinic Acid N-(3-Phenylpropan-1-ol-2-yl)amide 3.4 g of the intermediate compound 7b were introduced into 30 ml of methylene chloride in the presence of 4 ml of triethylamine and molecular sieve analogously to Example 5c and treated successively with 1.4 g of phenylalaninol, 1.1 g of HOBT and 2.0 g of EDC, 3.6 g (95%) of the product being obtained.

d) 2-(4-(Picol-4-yl)piperazin-1-yl)nicotinic Acid N-(3-phenylpropan-1-al-2-yl)amide 3.6 g of the intermediate compound 7c were oxidized using 4.4 g of $SO_3$-pyridine complex in 11 ml of DMSO and 80 ml of methylene chloride in the presence of 6 ml of triethylamine analogously to Example 1d, 0.9 g (25%) of the product being obtained in the form of the hydrochloride.

$^1$H NMR ($d_6$-DMSO): δ=2.7–3.9 (10H), 4.3–4.6 (3H), 7.0 (1H), 7.1–7.3 (3H), 7.4 (1H), 7.8–8.0 (2H), 8.3 (3H), 9.0 (3H), 9.7 (1H) ppm.

Example 8

2-(4-Benzylhomopiperazin-1-yl)nicotinic Acid N-(3-Phenylpropan-al-2-yl)amide a) 2-Chloronicotinic Acid N-(3-Phenylpropan-1-ol-2-yl)amide 10.0 g of chloronicotinic acid were reacted with 9.7 g of phenylalaninol in 250 ml of $CH_2Cl_2$ in the presence of 13.0 g of EDC, 2.9 g of HOBT and 9.6 g of triethylamine analogously to Example 1c, 17.3 g (94%) of the product being obtained.

b) 2-(4-Benzylhomopiperazin-1-yl)nicotinic Acid N-(3-Phenylpropan-1-ol-2-yl)amide 5.0 g of the intermediate compound 8a were treated with 3.3 g of benzylhomopiperazine, 4.8 g of potassium carbonate and a spatula tipful of 18-crown-6 in 70 ml of DMF and the mixture was heated to reflux for 2 h. The reaction mixture was poured onto water and extracted with ether. The combined organic extracts were washed with NaCl solution, dried over magnesium sulfate and concentrated. After MPLC purification, 1.0 g (13%) of the product were obtained.

c) 2-(4-Benzylhomopiperazin-1-yl)nicotinic Acid N-(3-Phenylpropan-1-al-2-yl)amide 1.0 g of the intermediate compound 8b were oxidized using 0.7 g of $SO_3$-pyridine complex in 20 ml of DMSO in the presence of 0.9 g of triethylamine analogously to Example 1d, 0.5 g (50%) of the product being obtained in the form of the free base.

$^1$H NMR ($CDCl_3$): δ=1.8 (2H), 2.6 (2H), 2.7 (2H), 3.2 (2H), 3.3 (2H), 3.4 (2H), 3.6 (2H), 4.9 (1H), 6.8 (1H), 7.1–7.3 (11H), 7.9 (1H), 8.3 (1H), 9.7 (1H) ppm.

Example 9

2-(4-(Picol-2-yl)homopiperazin-1-yl)nicotinic Acid N-(3-Phenylpropan-1-al-2-yl)amide a) Methyl 2-(4-(Picol-2-yl)homopiperazin-1-yl)nicotinate 2.4 g of methyl 2-chloronicotinate were reacted with 2.7 g of 2-picolylhomopiperazine in the presence of 3.8 g of potassium carbonate in 50 ml of DMF analogously to Example 1a, 3.7 g (81%) of the product being obtained.

b) 2-(4-(Picol-2-yl)homopiperazin-1-yl)nicotinic Acid 3.7 g of the intermediate compound 9a were hydrolyzed using 30 ml of 5M NaOH at 80° C. in 10 ml of THF analogously to Example 1b, 3.0 g (86%) of the product being obtained.

c) 2-(4-(Picol-2-yl)homopiperazin-1-yl)nicotinic Acid N-(3-Phenylpropan-1-ol-2-yl)amide 3.0 g of the intermediate compound 9b were dissolved in 60 ml of methylene chloride in the presence of 1.5 g of triethylamine analogously to Example 1c and the solution was treated successively with 1.5 g of phenylalaninol, 0.4 g of HOBT and 2.0 g of EDC, 2.7 g (62%) of the product being obtained.

d) 2-(4-(Picol-2-yl)homopiperazin-1-yl)nicotinic Acid N-(3-Phenylpropan-1-al-2-yl)amide 2.7 g of the intermediate compound 9c were oxidized using 2.9 g of SO$_3$-pyridine complex in the presence of 2.4 g of triethylamine in 10 ml of DMSO analogously to Example 1d, 2.2 g (83%) of the product being obtained in the form of the free base.

$^1$H NMR (CDCl$_3$): δ=1.8 (2H), 3.3–3.5 (8H), 3.7 (2H), 4.6 (1H), 6.7 (1H), 7.1–7.3 (2H), 7.4 (3H), 7.7 (2H), 8.1 (2H), 8.5 (2H), 9.6 (1H) ppm.

Example 10

2-(4-(Picol-4-yl)homopiperazin-1-yl)nicotinic Acid N-(3-Phenylpropan-1-al-2-yl)amide a) Methyl 2-(4-(Picol-4-yl)homopiperazin-1-yl)nicotinate 2.4 g of methyl 2-chloronicotinate were reacted with 2.6 g of 4-picolylhomopiperazine in the presence of 3.8 g of potassium carbonate in 50 ml of DMF analogously to Example 1a, 3.9 g (88%) of the product being obtained.

b) 2-(4-(Picol-4-yl)homopiperazin-1-yl)nicotinic Acid 3.9 g of the intermediate compound 10a were hydrolyzed at 80° C. using 40 ml of 5M NaOH in 20 ml of THF analogously to Example 1b, 2.7 g (70%) of the product being obtained.

c) 2-(4-(Picol-4-yl)homopiperazin-1-yl)nicotinic Acid N-(3-Phenylpropan-1-ol-2-yl)amide 2.6 g of the intermediate compound 10b were dissolved in 60 ml of methylene chloride in the presence of 1.7 g of triethylamine analogously to Example 1c and the solution was treated successively with 1.3 g of phenylalaninol, 0.4 g of HOBT and 1.7 g of EDC, 1.7 g (46%) of the product being obtained.

d) 2-(4-(Picol-4-yl)homopiperazin-1-yl)nicotinic Acid N-(3-Phenylpropan-1-al-2-yl)amide 1.7 g of the intermediate compound 10c were oxidized using 1.8 g of SO$_3$-pyridine complex in the presence of 1.6 g of triethylamine in 20 ml of DMSO analogously to Example 1d, 1.5 g (44%) of the product being obtained in the form of the free base.

$^1$H NMR (CDCl$_3$): δ=1.9 (2H), 2.6–2.8 (4H), 3.1–3.8 (8H), 4.7 (1H), 6.8 (1H), 7.0–7.4 (5H), 8.0 (1H), 8.2–8.3 (2H), 8.4–8.7 (4H), 9.8 (1H) ppm.

Example 11

2-(4-(2-Pyrid-2-yl)-1-ethyl)piperazin-1-yl)nicotinic Acid N-(3-Phenylpropan-1-al-2-yl)amide a) Methyl 2-(4-(2-Pyrid-2-yl)-1-ethyl)piperazin-1-yl)nicotinate 3.3 g of methyl 2-chloronicotinate were reacted in the presence of 4.3 g of potassium carbonate with 3.0 g of N-(2-(pyrid-2-yl)ethyl)piperazine in 20 ml of butanol analogously to Example 1a, 3.8 g (72%) of the product being obtained.

b) 2-(4-(2-Pyrid-2-yl)ethyl)piperazin-1-yl)nicotinic Acid 3.8 g of the intermediate compound 11a were hydrolyzed analogously to Example 5b for 1 h at 60° C. using 20 ml of 2M NaOH, 3.6 g of the still salt-containing product being obtained, which were employed in the next stage without further purification.

c) 2-(4-(2-Pyrid-2-yl)ethyl)piperazin-1-yl)nicotinic Acid N-(3-Phenylpropan-1-ol-2-yl)amide 3.6 g of the intermediate compound 11b were introduced into 50 ml of methylene chloride and 4 ml of DMF in the presence of 5.1 ml of triethylamine and molecular sieve analogously to Example 5c, and treated successively with 1.7 g of phenylalaninol, 1.4 g of HOBT and 2.5 g of EDC, 4.6 g (95%) of the product being obtained.

d) 2-(4-(2-Pyrid-2-yl)ethyl)piperazin-1-yl)nicotinic Acid N-(3-Phenylpropan-1-al-2-yl)amide 4.6 g of the intermediate compound 11c were oxidized using 3.5 g of SO$_3$-pyridine complex in 30 ml of methylene chloride and 15 ml of DMSO in the presence of 7.6 g of triethylamine analogously to Example 1d. The product was precipitated as the hydrochloride, 0.9 g (20%) of the product being obtained in the form of the hydrochloride.

$^1$H NMR (d$_6$-DMSO): δ=3.0–3.4 (8H), 3.4–3.7 (4H), 3.9–4.4 (3H), 7.1–7.5 (5H), 7.8 (2H), 7.9 (2H), 8.4 (3H), 8.8 (2H), 9.7 (1H) ppm.

Example 12

2-(4-(2-Methoxybenzyl)piperazin-1-yl)nicotinic Acid N-(3-Phenylpropan-1-al-2-yl)amide a) 2-(4-(2-Methoxybenzyl)piperazin-1-yl)nicotinic Acid N-(3-Phenylpropan-1-ol-2-yl)amide 3.0 g of intermediate compound 8a were reacted in 70 ml of DMF with 2.9 g of N-(2-methoxybenzyl)piperazine analogously to Example 8b in the presence of 5.7 g of potassium carbonate and a spatula tipful of 18-crown-6, 1.3 g (27%) of the product being obtained.

b) 2-(4-(2-Methoxybenzyl)piperazin-1-yl)nicotinic Acid N-(3-Phenylpropan-1-al-2-yl)amide 1.2 g of intermediate compound 12a were oxidized using 1.2 g of SO$_3$-pyridine complex in 20 ml of DMSO in the presence of 1.1 g of triethylamine analogously to Example 1d, 0.7 g (58%) of the product being obtained in the form of the free base.

MS: m/e=458 (M$^+$).

Example 13

2-(4-(3,4-Dioxomethylenebenzyl)piperazin-1-yl)nicotinic Acid N-(3-Phenylpropan-1-al-2-yl)amide a) 2-(4-(3,4-Dioxomethylenebenzyl)piperazin-1-yl)nicotinic Acid N-(3-Phenylpropan-1-ol-2-yl)amide 3.0 g of intermediate compound 8a in 70 ml of DMF were reacted with 2.3 g of N-(3,4-dioxomethylenebenzyl)piperazine analogously to Example 8b in the presence of 2.9 g of potassium carbonate and a spatula tipful of 18-crown-6, 1.3 g (27%) of the product being obtained.

b) 2-(4-(3,4-Dioxomethylenebenzyl)piperazin-1-yl)nicotinic Acid N-(3-Phenylpropan-1-al-2-yl)amide 0.6 g of intermediate compound 13a were oxidized using 0.6 g of SO$_3$-pyridine complex in 20 ml of DMSO in the presence of 0.5 g of triethylamine analogously to Example 1d, 0.3 g (55%) of the product being obtained in the form of the free base.

$^1$H NMR (CDCl$_3$): δ=2.3 (2H), 2.4 (2H), 3.0–3.2 (4H), 3.3–3.4 (4H), 4.9 (1H), 5.9 (2H), 6.7 (2H), 6.8 (1H), 7.1–7.3 (7H), 8.4 (2H), 9.8 (1H) ppm.

Example 14

2-(4-(1-Piperidinyl)piperidin-1-yl)nicotinic Acid N-(3-Phenylpropan-1-al-2-yl)amide a) Methyl 2-(4-(1-Piperidinyl)piperidin-1-yl)nicotinate 3.4 g of methyl 2-chloronicotinate were reacted with 3.4 g of 4-piperidinopideridine in 75 ml of DMF in the presence of 5.5 g of potassium carbonate and a spatula tipful of 18-crown-6 analogously to Example 1a, 5.9 g (97%) of the product being obtained.

b) 2-(4-(1-Piperidinyl)piperidin-1-yl)nicotinic Acid 5.5 g of the intermediate compound 14a in 100 ml of THF were reacted with 1.3 g of LiOH in 50 ml of water and 10 ml of MeOH analogously to Example 1b, 8.1 g of the still salt-containing product being obtained, which were employed directly in the next stage without further purification.

c) 2-(4-(1-Piperidinyl)piperidin-1-yl)nicotinic Acid N-(3-Phenylpropan-1-ol-2-yl)amide 7.1 g of the intermediate compound 14b were introduced into 200 ml of methylene chloride and 50 ml of DMF in the presence of 5.2 g of triethylamine and 5 g of sodium sulfate analogously to Example 1c and treated successively with 2.6 g of phenylalaninol, 2.3 g of HOBT and 3.6 g of EDC, 0.7 g (10%) of the product being obtained.

d) 2-(4-(1-Piperidinyl)piperidin-1-yl)nicotinic Acid N-(3-Phenylpropan-1-al-2-yl)amide 0.6 g of the intermediate compound 14c was oxidized using 1.0 g of $SO_3$-pyridine complex in the presence of 0.6 g of triethylamine in 20 ml of DMSO analogously to Example 1d, 0.1 g (19%) of the product being obtained in the form of the free base.

MS: m/e=420 ($M^+$).

Example 15

2-(4-(4-N,N-Dimethylamino)benzylhomopiperazin-1-yl)nicotinic Acid N-(3-Phenylpropan-1-al-2-yl)amide a) Ethyl 2-(Homopiperazin-1-yl)nicotinate 10.0 g of ethyl 2-chloronicotinate were heated to reflux for 2 h with 21.6 g of homopiperazine in 150 ml of ethanol. After removing the solvent, the residue was partitioned between NaCl solution and ethyl acetate and the aqueous phase was extracted several times with ethyl acetate. The combined organic phases were dried over magnesium sulfate and concentrated, 11.1 g (83%) of the product being obtained.

b) Ethyl 2-(4-(4-N,N-Dimethylaminobenzyl)homopiperazin-1-yl)nicotinate 2.0 g of the intermediate compound 18a and 1.3 g of 4-N,N-dimethylaminobenzaldehyde were introduced into 40 ml of ethanol and treated at room temperature with 1.1 ml of borane-pyridine complex. The mixture was stirred at room temperature for 18 h. After removing the solvent, the residue was partitioned between water and ethyl acetate. The organic phase was extracted with 2N HCl, and the aqueous phase was washed twice with ethyl acetate and rendered basic with 2N NaOH. The product was extracted with ethyl acetate, and the combined ethyl acetate extracts were dried over magnesium sulfate and concentrated, 2.9 g (93%) of the product being obtained.

c) 2-(4-(4-N,N-Dimethylaminobenzyl)homopiperazin-1-yl)nicotinic Acid 2.8 g of the intermediate compound 18b were heated at 60° C. for 2 h with 30 ml of 5N NaOH in 30 ml of MeOH. After concentrating the solvent, the mixture was neutralized with conc. HCl, salted out using EtOH and triethylamine, the salt was filtered off and the filtrate was concentrated, 2.5 g (100%) of the product being obtained.

d) 2-(4-(4-N,N-Dimethylaminobenzyl)homopiperazin-1-yl)nicotinic Acid N-(3-Phenylpropan-1-ol-2-yl)amide 2.3 g of the intermediate compound 18c were dissolved in 50 ml of methylene chloride and treated successively with 0.8 g of triethylamine, 0.6 g of phenylalaninol, 0.2 g of HOBT and 0.8 g of EDC. The mixture was stirred at room temperature for 5 h over molecular sieve. The reaction mixture was washed with water and 2N NaOH and the product was extracted with 1N HCl. The aqueous phase was washed with ethyl acetate and adjusted to pH 9 using 2N NaOH. The product was extracted with ethyl acetate. The combined organic phases were dried over magnesium sulfate and concentrated, 1.2 g (69%) of the product being obtained.

e) 2-(4-(4-N,N-Dimethylaminobenzyl)homopiperazin-1-yl)nicotinic Acid N-(3-Phenylpropan-1-al-2-yl)amide 1.2 g of intermediate 18d were stirred over molecular sieve with 1.2 g of $SO_3$-pyridine complex in the presence of 1.0 g of triethylamine and 2 ml of DMSO in 40 ml of methylene chloride. The reaction mixture was diluted with methylene chloride, washed three times with NaCl, dried over magnesium sulfate and concentrated, 1.1 g (97%) of the product being obtained.

$^1$H NMR ($CDCl_3$): δ=1.8 (2H), 3.0 (6H), 3.1 (4H), 3.2 (4H), 3.4 (2H), 4.4 (2H), 4.8 (1H), 6.6 (3H), 6.8 (1H), 7.2 (5H), 8.0 (1H), 8.2 (1H), 8.7 (1H), 9.8 (1H) ppm.

Example 16

2-(4-(2-Fluorobenzyl)piperazin-1-yl)nicotinic Acid N-(3-Phenylpropan-1-al-2-yl)amide a) Ethyl 2-(Piperazin-1-yl)nicotinate 10.0 g of ethyl 2-chloronicotinate were reacted with 27.8 g of piperazine in 400 ml of ethanol analogously to Example 18a, 6.9 g (54%) of the product being obtained.

b) Ethyl 2-(4-(2-Fluorobenzyl)piperazin-1-yl)nicotinate 1.0 g of the intermediate compound 19a were reacted with 2-fluorobenzaldehyde and 0.5 g of borane-pyridine complex in 40 ml of ethanol analogously to Example 18b, 1.2 g (39%) of the product being obtained.

c) 2-(4-(2-Fluorobenzyl)piperazin-1-yl)nicotinic Acid 1.2 g of the intermediate compound 19b were dissolved in 15 ml of methanol and hydrolyzed using 30 ml of 5N NaOH analogously to Example 18c, 0.7 g (63%) of the product being obtained.

d) 2-(4-(2-Fluorobenzyl)piperazin-1-yl)nicotinic Acid N-(3-Phenylpropan-1-ol-2-yl)amide 0.7 g of the intermediate compound 19c was introduced into 50 ml of methylene chloride in the presence of 0.5 g of triethylamine analogously to Example 18d and treated successively with 0.3 g of phenylalaninol, 0.5 g of EDC and 0.1 g of HOBT 0.5 g (48%) of the product being obtained.

e) 2-(4-(2-Fluorobenzyl)piperazin-1-yl)nicotinic Acid N-(3-Phenylpropan-1-al-2-yl)amide 0.5 g of the intermediate compound 19d was oxidized using 0.5 g of $SO_3$-pyridine complex in 40 ml of methylene chloride and 1 ml of DMSO in the presence of 0.4 g of triethylamine analogously to Example 18e, 0.5 g (100%) of the product being obtained.

MS: m/e=446 ($M^+$).

Example 17

2-(4-Phenylpiperazin-1-yl)nicotinic Acid N-(3-Phenylpropan-1-al-2-yl)amide a) Ethyl 2-(4-Phenylpiperazin-1-yl)nicotinate 2.0 g of ethyl 2-chloronicotinate were reacted at 80° C. for 2.5 h with 1.8 g of phenylpiperazine in the presence of 2.5 g of potassium carbonate and a spatula tipful of 18-crown-6 in 40 ml of butanol analogously to Example 1a, 1.2 g (35%) of the product being obtained.

b) 2-(4-Phenylpiperazin-1-yl)nicotinic Acid 1.2 g of the intermediate compound 20a were hydrolyzed using 30 ml of 5M NaOH in 30 ml of methanol analogously to Example 18c, 1.8 g of the crude product being obtained, which were employed in the next stage without further purification.

c) 2-(4-Phenylpiperazin-1-yl)nicotinic Acid N-(3-Phenylpropan-1-ol-2-yl)amide 1.8 g of the intermediate compound 20b were introduced into 50 ml of methylene chloride in the presence of 0.8 g of triethylamine analogously to Example 18d and treated successively with 0.6 g of phenylalaninol, 0.8 g of EDC and 0.2 g of HOBT, 1.1 g (72%) of the product being obtained.

d) 2-(4-Phenylpiperazin-1-yl)nicotinic Acid N-(3-Phenylpropan-1-al-2-yl)amide 1.1 g of the intermediate compound 20c were oxidized using 1.2 g of $SO_3$-pyridine complex in 40 ml of methylene chloride and 2 ml of DMSO in the presence of 1.1 g of triethylamine analogously to Example 18e, 0.8 g (72%) of the product being obtained.

MS: m/e=414 ($M^+$).

Example 18

2-(4-(Picol-2-yl)homopiperazin-1-yl)nicotinic Acid N-(1-Carbamoyl-1-oxo-3-phenylpropan-2-yl)amide a) 2-(4-(Picol-2-yl)homopiperazin-1-yl)nicotinic Acid N-(1-Carbamoyl-1-ol-3-phenylpropan-2-yl)amide 1.8 g of the intermediate compound 9b were introduced into 50 ml of methylene chloride in the presence of 1.9 g of triethylamine analogously to Example 18d and treated successively with 1.1 g of 3-amino-2-hydroxy-4-phenylbutyramide hydrochloride, 1.2 g of EDC and 0.3 g of HOBT, 0.5 g (18%) of the product being obtained.

b) 2-(4-(Picol-2-yl)homopiperazin-1-yl)nicotinic Acid N-(1-Carbamoyl-1-oxo-3-phenylpropan-2-yl)amide 0.5 g of the intermediate compound 21a was oxidized using 0.4 g of $SO_3$-pyridine complex in 40 ml of methylene chloride and 2.5 ml of DMSO in the presence of 0.4 g of triethylamine analogously to Example 18e, 0.2 g (54%) of the product being obtained.

MS: m/e=486 ($M^+$).

Example 19

2-(4-(4-Methoxybenzyl)piperazin-1-yl)nicotinic Acid N-(3-Phenylpropan-1-al-2-yl)amide a) Ethyl 2-(4-(4-Methoxybenzyl)piperazin-1-yl)nicotinate 2.0 g of the intermediate compound 19a were reacted with 6.0 ml of anisaldehyde and 1.1 ml of borane-pyridine complex in 40 ml of ethanol analogously to Example 18b, 3.0 g (94%) of the product being obtained.

b) 2-(4-(4-Methoxybenzyl)piperazin-1-yl)nicotinic Acid 1.5 g of the intermediate compound 22a were hydrolyzed using 25 ml of 5M NaOH in 10 ml of methanol analogously to Example 18c, 1.6 g (61%) of the product being obtained.

c) 2-(4-(4-Methoxybenzyl)piperazin-1-yl)nicotinic Acid N-(3-Phenylpropan-1-ol-2-yl)amide 1.0 g of the intermediate compound 22b were introduced into 50 ml of methylene chloride in the presence of 1.4 ml of triethylamine analogously to Example 18d and treated successively with 0.5 g of phenylalaninol, 0.8 g of EDC and 0.5 g of HOBT, 1.2 g (88%) of the product being obtained.

d) 2-(4-(4-Methoxybenzyl)piperazin-1-yl)nicotinic Acid N-(3-Phenylpropan-1-al-2-yl)amide 1.2 g of the intermediate compound 22c were oxidized using 3.0 g of $SO_3$-pyridine complex in 50 ml of methylene chloride in 3.5 ml of DMSO in the presence of 2.1 ml of triethylamine analogously to Example 18e, 0.5 g (46%) of the product being obtained.

MS: m/e=458 ($M^+$).

Example 20

2-(4-(4-Methoxybenzyl)homopiperazin-1-yl) nicotinic Acid N-(3-Phenylpropan-1-al-2-yl)amide a) Ethyl 2-(4-(4-Methoxybenzyl)homopiperazin-1-yl)nicotinate 2.5 g of the intermediate compound 18a were reacted with 1.4 ml of anisaldehyde and 1.3 ml of borane-pyridine complex in 30 ml of ethanol analogously to Example 18b, 3.6 g (98%) of the product being obtained.

b) 2-(4-(4-Methoxybenzyl)homopiperazin-1-yl)nicotinic Acid 3.6 g of the intermediate compound 23a were hydrolyzed using 20 ml of 5M NaOH in 10 ml of methanol analogously to Example 18c, 2.9 g (87%) of the product being obtained.

c) 2-(4-(4-Methoxybenzyl)homopiperazin-1-yl)nicotinic Acid N-(3-Phenylpropan-1-ol-2-yl)amide 1.3 g of the intermediate compound 23b were introduced into 50 ml of methylene chloride in the presence of 1.75 g of triethylamine analogously to Example 18d and treated successively with 0.6 g of phenylalaninol, 0.9 g of EDC and 0.6 g of HOBT, 1.3 g (69%) of the product being obtained.

d) 2-(4-(4-Methoxybenzyl)homopiperazin-1-yl)nicotinic Acid N-(3-Phenylpropan-1-al-2-yl)amide 1.2 g of the intermediate compound 23c were oxidized using 3.0 g of $SO_3$-pyridine complex in 50 ml of methylene chloride and 3.5 ml of DMSO in the presence of 2.1 ml of triethylamine analogously to Example 18e, 0.6 g (46%) of the product being obtained.

MS: m/e=472 ($M^+$).

Example 21

2-(4-(4-n-Butoxybenzyl)piperazin-1-yl)nicotinic Acid N-(3-Phenylpropan-1-al-2-yl)amide a) Ethyl 2-(4-(4-n-Butoxybenzyl)piperazin-1-yl)nicotinate 2.4 g of the intermediate compound 19a were reacted with 2.1 ml of 4-butoxybenzaldehyde and 1.3 ml of borane-pyridine complex in 30 ml of ethanol analogously to Example 18b, 3.5 g (89%) of the product being obtained.

b) 2-(4-(4-n-Butoxybenzyl)piperazin-1-yl)nicotinic Acid 3.5 g of the intermediate compound 24a were hydrolyzed using 15 ml of 5M NaOH in 30 ml of methanol analogously to Example 18c, 3.2 g (97%) of the product being obtained.

c) 2-(4-(4-n-Butoxybenzyl)piperazin-1-yl)nicotinic Acid N-(3-Phenylpropan-1-ol-2-yl)amide 1.5 g of the intermediate compound 24b were introduced into 50 ml of methylene chloride in the presence of 1.9 ml of triethylamine analogously to Example 18d and treated successively with 0.7 g of phenylalaninol, 1.0 g EDC and 0.7 g of HOBT, 1.3 g (62%) of the product being obtained.

d) 2-(4-(4-n-Butoxybenzyl)piperazin-1-yl)nicotinic Acid N-(3-Phenylpropan-1-al-2-yl)amide 1.3 g of the intermediate compound 24c were oxidized using 2.0 g of $SO_3$-pyridine complex in 40 ml of methylene chloride and 3.5 ml of DMSO in the presence of 2.1 ml of triethylamine analogously to Example 18e, 0.8 g (52%) of the product being obtained.

MS: m/e=500 ($M^+$).

Example 22

3-(4-Benzylpiperazin-1-yl)benzoic Acid N-(1-Carbamoyl-1-oxo-3-phenylpropan-2-yl)amide a) 3-(4-Benzylpiperazin-1-yl)benzoic Acid 1.5 g of 3-benzylpiperazin-1-ylbenzonitrile were heated to reflux for 2 h in 14 ml of conc. HCl. On cooling to room temperature, 1.7 g (100%) of the product precipitated, which were filtered off with suction and washed thoroughly with water.

b) 3-(4-Benzylpiperazin-1-yl)benzoic Acid N-(1-carbamoyl-1-ol-3-phenylpropan-2-yl)amide 1.5 g of the intermediate compound 26a were introduced into 50 ml of DMF analogously to Example 1c in the presence of 2.9 ml of triethylamine and treated successively with 0.7 g of HOBT, 1.2 g of 3-amino-2-hydroxy-4- phenylbutyramide hydrochloride and 1.1 g of EDC, 1.7 g (71%) of the product being obtained.

c) 3-(4-Benzylpiperazin-1-yl)benzoic Acid N-(1-Carbamoyl-1-oxo-3-phenylpropan-2-yl)amide 1.5 g of the intermediate compound 26b were dissolved in 30 ml of DMSO and oxidized using 1.5 g of $SO_3$-pyridine complex in the presence of 2 ml of triethylamine analogously to Example 1d, 0.5 g (33%) of the product being obtained.

MS: m/e=470 ($M^+$).

Example 23

2-(4-(2-Naphtylmethyl)piperazin-1-yl)nicotinic Acid N-(3-Phenylpropan-1-al-2-yl)amide a) 2-(4-Butoxycarbonylpiperazin-1-yl)nicotinic Acid N-(3-Phenylpropan-1-ol-2-yl)amide 13 g of 2-(4-butoxycarbonylpiperazin-1-yl)nicotinic acid were dissolved in 150 ml of methylene chloride and 14.7 ml of triethylamine analogously to Example 1c and treated successively with 6.4 g of phenylalaninol, 1.9 g of HOBT and 8.11 g of EDC, 16.7 g (90%) of the product being obtained.

b) 2-(Piperazin-1-yl)nicotinic Acid N-(3-Phenylpropan-1-ol-2-yl)amide 16.7 g of the intermediate compound 27a were dissolved in 300 ml of methylene chloride and treated with 30 ml of conc. trifluoroacetic acid. The mixture was stirred at room temperature for 1.5 h. The reaction mixture was poured onto ice water, rendered basic and the product was extracted with methylene chloride. The combined organic phases were dried over magnesium sulfate and concentrated, 12.8 g (98%) of the product being obtained.

c) 2-(4-(2-Naphtylmethyl)piperazin-1-yl)nicotinic Acid N-(3-Phenylpropan-1-ol-2-yl)amide 1.9 g of the intermediate compound 27b were introduced into 75 ml of ethanol and treated with 1.3 g of 2-α-bromomethylnaphthalene and 0.8 g of potassium carbonate. The mixture was stirred at room temperature for 18 h. The reaction mixture was concentrated, the residue was partitioned between ethyl acetate and water and the organic phase was dried over magnesium sulfate and concentrated, 2.3 g (86%) of the product being obtained.

d) 2-(4-(2-Naphtylmethyl)piperazin-1-yl)nicotinic Acid N-(3-Phenylpropan-1-al-2-yl)amide 1.5 g of the intermediate compound 27c were oxidized using 1.5 g of $SO_3$-pyridine complex in 25 ml of DMSO in the presence of 1.7 ml of triethylamine analogously to Example 1d, 0.9 g (59%) of the product being obtained.

MS: m/e=478 ($M^+$).

Example 24

2-(4-(2-Tolyl)piperazin-1-yl)nicotinic Acid N-(3-Phenylpropan-1-al-2-yl)amide a) 2-(4-(2-Tolyl)piperazin-1-yl)nicotinic Acid N-(3-Phenylpropan-1-ol-2-yl)amide 2.0 g of the intermediate compound 27 were introduced into 100 ml of ethanol analogously to Example 27c and treated with 1.1 g of 2-(bromomethyl)toluene and 0.8 g of potassium carbonate, 1.6 g (62%) of the product being obtained.

b) 2-(4-(2-Tolyl)piperazin-1-yl)nicotinic Acid N-(3-Phenylpropan-1-al-2-yl)amide 1.4 g of the intermediate compound 28a were oxidized using 1.0 g of $SO_3$-pyridine complex in 25 ml of DMSO in the presence of 1.7 ml of triethylamine analogously to Example 1d, 0.7 g (48%) of the product being obtained.

MS: m/e=460 ($M^+$+$H_2O$).

Example 25

2-(4-(3-Tolyl)piperazin-1-yl)nicotinic Acid N-(3-Phenylpropan-1-al-2-yl)amide a) 2-(4-(3-Tolyl)piperazin-1-yl)nicotinic Acid N-(3-Phenylpropan-1-ol-2-yl)amide 2.0 g of the intermediate compound 29b were introduced into 80 ml of ethanol analogously to Example 27c and treated with 1.1 g of 3(bromomethyl)toluene and 0.8 g of potassium carbonate, 1.8 g (70%) of the product being obtained.

b) 2-(4-(3-Tolyl)piperazin-1-yl)nicotinic Acid N-(3-Phenylpropan-1-al-2-yl)amide 1.6 g of the intermediate compound 29a were oxidized using 1.2 g of $SO_3$-pyridine complex in 25 ml of DMSO in the presence of 2.0 ml of triethylamine analogously to Example 1d, 0.4 g (26%) of the product being obtained.

MS: m/e=442 ($M^+$).

Example 26

2-(4-(4-Tolyl)piperazin-1-yl)nicotinic Acid N-(3-Phenylpropan-1-al-2-yl)amide a) 2-(4-(4-Tolyl)piperazin-1-yl)nicotinic Acid N-(3-Phenylpropan-1-ol-2-yl)amide 1.6 g of the intermediate compound 27b were introduced into 80 ml of ethanol analogously to Example 27c and treated with 1.1 g of 4(bromomethyl)toluene and 0.8 g of potassium carbonate, 1.8 g (69%) of the product being obtained.

b) 2-(4-(4-Tolyl)piperazin-1-yl)nicotinic Acid N-(3-Phenylpropan-1-al-2-yl)amide 1.6 g of the intermediate compound 30a were oxidized using 1.2 g of $SO_3$-pyridine complex in 25 ml of DMS0 in the presence of 2.0 ml of triethylamine analogously to Example 1d, 0.7 g (46%) of the product being obtained.

MS: m/e=460 ($M^+$+$H_2O$).

Example 27

2-(4-(4-Methoxycarbonylbenzylpiperazin-1-yl) nicotinic Acid N-(3-Phenylpropan-1-al-2-yl)amide a) 2-(4-(4-Methoxycarbonylbenzylpiperazin-1-yl)nicotinic Acid N-(3-Phenylpropan-1-ol-2-yl)amide 2.5 g of the intermediate compound 27b were introduced into 100 ml of ethanol analogously to Example 27c and treated with 1.7 g of methyl bromomethylbenzoate and 1.0 g of potassium carbonate, 1.9 g (54%) of the product being obtained.

b) 2-(4-(4-Methoxycarbonylbenzylpiperazin-1-yl)nicotinic Acid N-(3-Phenylpropan-1-al-2-yl)amide 0.9 g of the intermediate compound 31a was oxidized using 0.6 g of $SO_3$-pyridine complex in 5 ml of DMSO in the presence of 1.0 ml of triethylamine analogously to Example 1d, 0.1 g (15%) of the product being obtained.

MS: m/e=485 ($M^+$−1).

The following examples were synthesized analogously to Examples 1–27:

Example 28

2-(4-Picol-3-yl)homopiperazin-1-yl)nicotinic Acid N-(3-Phenylpropan-1-al-2-yl)amide MS: m/e=443 ($M^+$).

Example 29

2-(4-Benzylpiperazin-1-yl)nicotinic Acid N-(1-Carbamoyl-1-oxo-3-phenylpropan-2-yl)amide Dihydrochloride MS: m/e=471 ($M^+$).

Example 30

2-(4-Benzylpiperazin-1-yl)benzoic Acid N-(1-Carbamoyl-1-oxo-3-phenylpropan-2-yl)amide MS: m/e=470 (M⁺).

Example 31

2-(4-Benzylpiperazin-1-yl)nicotinic Acid N-(1-Carbamoyl-1-oxohexan-2-yl)amide

MS: m/e=437 (M⁺).

Example 32

2-(4-Benzylpiperazin-1-yl)pyridin-4-carboxylic Acid N-(3-Phenylpropan-1-al-2-yl)amide MS: m/e=428 (M⁺).

Example 33

2-(4-Benzylpiperazin-1-yl)nicotinic Acid N-(N(2-Piperidin-1-yl-1-ethyl)-1-carbamoyl-1-oxo-3-phenylpropan-2-yl)amide MS: m/e=582 (M⁺).

Example 34

2-(4-Benzylpiperazin-1-yl)nicotinic Acid N-(N(2-Piperidin-1-yl-1-ethyl)-1-carbamoyl-1-oxo-3-phenylpropan-2-yl)amide MS: m/e=584 (M⁺).

Example 35

2-(4-Benzylpiperazin-1-yl)nicotinic Acid N-(N(2-Pyrid-2-yl-1-ethyl)-1-carbamoyl-1-oxo-3-phenylpropan-2-yl)amide MS: m/e=576 (M⁺).

Example 36

2-(4-Benzylpiperazin-1-yl)nicotinic Acid N-(3(4-Methyl piperazin-1-yl)-1-propyl)-1-carbamoyl-1-oxo-3-phenylpropan-2-yl)-amide MS: m/e=611 (M⁺).

Example 37

2-(4-Benzylpiperazin-1-yl)nicotinic Acid N-(N(3(N,N-Diethylamino-1-propyl)-1-carbamoyl-1-oxo-3-phenylpropan-2-yl)amide MS: m/e=584 (M⁺).

Example 38

2-((3-N,N-Dimethylaminomethylpyrid-2-yl)piperazin-1-yl)nicotinic Acid N-(3-Phenylpropan-1-al-2-yl)amide x Trifumaric Acid MS: m/e=500 (M⁺+1).

Example 39

2-(4-Phenylpiperazin-1-yl)benzoic Acid N-(1-Carbamoyl-1-oxo-3-phenylpropan-2-yl)amide MS: m/e=456 (M⁺).

Example 40

5-Nitro-2-(4-phenylpiperazin-1-yl)benzoic Acid N-(1-Carbamoyl-1-oxo-3-phenylpropan-2-yl)amide MS: m/e=501 (M⁺).

Example 41

2-(4-Benzylpiperazin-1-yl)-5-nitrobenzoic Acid N-(1-Carbamoyl-1-oxo-3-phenylpropan-2-yl)amide MS: m/e=515 (M⁺).

Example 42

2-(3-Phenylpyrrolidin-1-yl)nicotinic Acid N-(1-Carbamoyl-1-oxo-3-phenylpropan-2-yl)amide

| ¹H-NMR (CF₃COOD): δ = | 2.0–2.7 (2H); 3.0 (1H); 3.3–4.0 (6H); 5.9 (1H); 6.9 (1H), 7.0–7.4 (10H) and 7.9 (2H) ppm |
|---|---|

Example 43

2(4(4(N,N-Dimethylamino)benzylpiperazin-1-yl))nicotinic Acid N-(3-Phenylpropan-1-al-2-yl)amide MS: m/e=471.

Example 44

2-(4(3(2-(N,N-Diethylamino)-1-ethylpyrid-2-yl)piperazin-1-yl)-nicotinic Acid N-(1-Carbamoyl-1-oxo-3-phenylpropan-2-yl)amide

| ¹H-NMR (Methanol-D₄): δ = | 1.4(6H); 3.0–4.0 (17H); 4.5 (2H); 7.0–7.5 (7H); 8.0–9.0 (5H) |
|---|---|

Example 45

4-(4-Benzylpiperazin-1-yl)nicotinic Acid N-(1-Carbamoyl-1-oxo-3-phenylpropan-2-yl)amide MS: m/e=471.

Example 46

2-(4-Pyrid-2-yl)piperazin-1-yl)nicotinic Acid N-(3-Phenylpropan-1-al-2-yl)amide

MS: m/e=415.

Example 47

2-(4-(Pyrid-2-yl)piperazin-1-yl)nicotinic Acid N-(1-Carbamoyl-1-oxo-3-phenylpropan-2-yl)amide

| ¹H-NMR (DMSO-D₆): δ = | 2.9–4.1 (10H); 5.5 (1H); 6.7–8.2 (14H); 9.1 (1H) |
|---|---|

Example 48

2-(4-Benzylpiperazin-1-yl)nicotinic Acid N-(Pentan-1-al-2-yl)amide

| $^1$H-NMR (CDCl$_3$): δ = | 1.0–2.0 (7H); 2.7–3.8 (8H); 4.8 (1H); 7.3–8.4 (8H); 9.7 (2H) |
|---|---|

Example 49

2-(4-Benzylpiperazin-1-yl)nicotinic Acid N-(3-(Indol-3-yl)propan-1-al-2-yl)amide

| $^1$H-NMR (CDCl$_3$): δ = | 2.0–3.5 (12H); 5.0 (1H); 7.3–8.0 (13H); 8.4 (2H); 9.6–9.8 (2H) |
|---|---|

Example 50

2-(4-(Picol-2-yl)homopiperazin-1-yl)nicotinic Acid N-(3-(Indol-3-yl)propan-1-al-2-yl)amide

| $^1$H-NMR (CDCl$_3$): δ = | 1.7 (2H); 2.6–3.7 (12H); 5.0 (1H); 6.8–8.6 (14H); 9.8 (1H) |
|---|---|

Example 51

2-(4-Benzylpiperazin-1-yl)pyridin-4-carbonxylic Acid N(1-Carbamoyl-1-oxo-3-phenylpropan-2-yl)amide MS: m/e=471.

Example 52

2-(4-Methylpiperazin-1-yl)quinoline-4-carboxylic Acid-N-(1-carbamoyl-1-oxo-3-phenylpropan-2-yl)amide

| $^1$H-NMR (D$_2$O): δ = | 2.8 (1H); 3.0 (3H); 3.2–4.5 (9H); 6.7–7.8 (10H) |
|---|---|

Example 53

2-(4-Benzylhomopiperazin-1-yl)pyridine-4-carboxylic Acid N-(3-Phenylpropan-1-al-2-yl)amide MS: m/e=442.

TABLE

| No. | $\underset{R^2}{\overset{O}{\underset{R^1}{\parallel}}}\!\!\!\!\!\!\!\!\!\!\!\!\!\!\!\!\!\!\!\!\!\!\!\!\!\!\!$ C—B | (CH$_2$)$_x$—A | R$^5$ | R$^3$ | R$^4$ |
|---|---|---|---|---|---|
| 1 | 3-pyridyl C(=O) | piperazinyl-N-R$^5$ | 4-ethyl-N,N-diethylaniline | benzyl (CH) | H |
| 2 | 3-pyridyl C(=O) | piperazinyl-N-R$^5$ | 4-ethyl-N,N-diethylaniline | benzyl (CH) | CONH$_2$ |
| 3 | 3-pyridyl C(=O) | piperazinyl-N-R$^5$ | 4-ethyl-4-ethoxyphenyl | benzyl (CH) | H |
| 4 | 3-pyridyl C(=O) | piperazinyl-N-R$^5$ | 2-ethyl-nitrobenzene | phenethyl | H |

TABLE-continued
| No. | 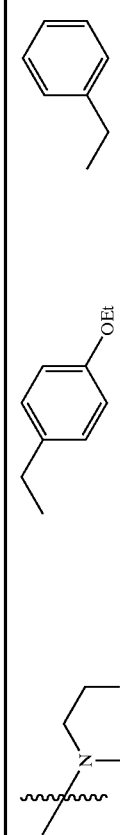 | (CH$_2$)$_x$—A | R$^5$ | R$^3$ | R$^4$ |
|---|---|---|---|---|---|
| 5 | 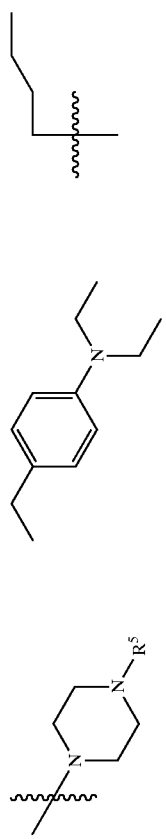 | 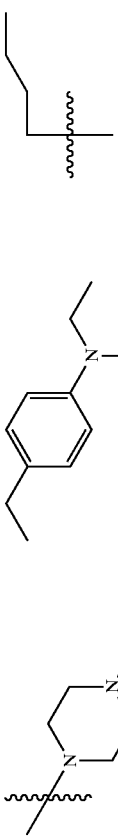 | 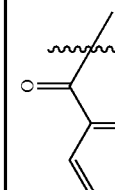 | 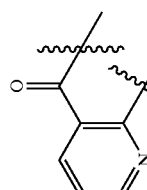 | CONH$_2$ |
| 6 | 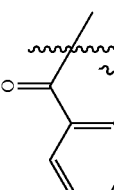 | 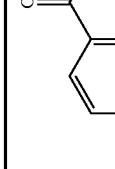 | 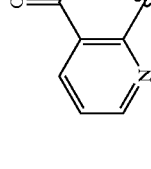 | 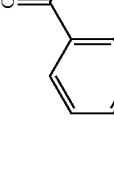 | H |
| 7 | 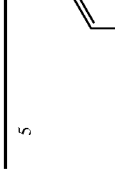 | 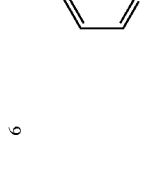 |  | | CONH$_2$ |
| 8 | | | | | H |

TABLE-continued

| No. | ![structure] | (CH$_2$)$_x$—A | R$^5$ | R$^3$ | R$^4$ |
|---|---|---|---|---|---|
| 9 | 3-carbonyl-pyridin-2-yl | N-methylpiperazinyl (N-R$^5$) | 4-ethyl-phenyl with NO$_2$ | benzyl | H |
| 10 | 3-carbonyl-pyridin-2-yl | N-methylpiperazinyl (N-R$^5$) | 2-ethyl-phenyl with NMe$_2$ | benzyl | CONH$_2$ |
| 11 | 3-carbonyl-pyridin-2-yl | N-methylpiperazinyl (N-R$^5$) | 4-ethyl-phenyl with NMe$_2$ | benzyl | CONH$_2$ |
| 12 | 3-carbonyl-pyridin-2-yl | N-methylpiperazinyl (N-R$^5$) | 2-ethyl-phenyl with NMe$_2$ | benzyl | H |

TABLE-continued

| No. | $\overset{O}{\underset{R^1\ R^2}{\|\|}}\underset{}{\overset{C}{\underset{B}{\|}}}$ | (CH$_2$)$_x$—A | R$^5$ | R$^3$ | R$^4$ |
|---|---|---|---|---|---|
| 13 | 3-pyridinoyl | N-methylpiperazinyl | 2-ethyl-6-NMe$_2$-phenyl | benzyl (PhCH$_2$CH$_2$-) | CONH$_2$ |
| 14 | 3-pyridinoyl | N-methylpiperazinyl | 2-ethyl-6-NMe$_2$-phenyl | pentyl | H |
| 15 | 3-pyridinoyl | N-methylpiperazinyl | 4-ethyl-2-NO$_2$-phenyl | benzyl | CONH$_2$ |
| 16 | 3-pyridinoyl | N-methylpiperazinyl | 4-ethyl-2-NO$_2$-phenyl | benzyl | CONH$_2$ |

TABLE-continued
| No. | $\begin{array}{c}O\\\|\\R^1-B-C\\\|\\R^2\end{array}$ | $-(CH_2)_x-A$ | $R^5$ | $R^3$ | $R^4$ |
|---|---|---|---|---|---|
| 17 | 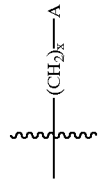 | 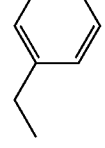 | 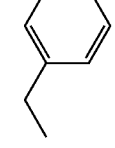 | 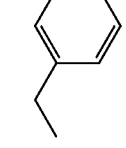 | H |
| 18 | 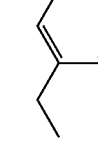 | 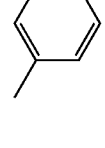 | 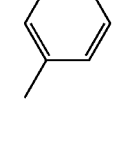 | 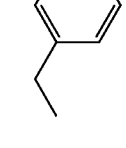 | $CONH_2$ |
| 19 | 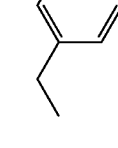 |  |  |  | H |
| 20 |  | 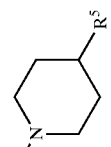 | 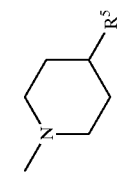 | 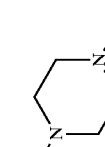 | $CONH_2$ |
| 21 | 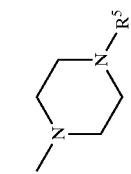 | 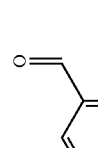 | 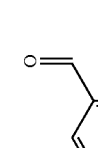 | 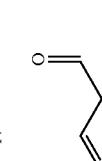 | H |

TABLE-continued

| No. | ![structure with R¹, R², B, C and C=O] | ‍$-(CH_2)_x-A$ | $R^5$ | $R^3$ | $R^4$ |
|---|---|---|---|---|---|
| 22 | 4-methylpyridin-3-yl carbonyl | 4-methylpiperazin-1-yl (N-R⁵) | benzyl | benzyl | CONH$_2$ |
| 23 | 2-methylpyridin-3-yl carbonyl | 1-methylpiperidin-4-yl | benzyl | 4-hydroxybenzyl | H |
| 24 | 2-methylpyridin-3-yl carbonyl | 1-methylpiperidin-4-yl | benzyl | isopropyl | H |
| 25 | 2-methylpyridin-3-yl carbonyl | 1-methylpiperidin-4-yl | benzyl | cyclohexylmethyl | H |
| 26 | 2-methylpyridin-3-yl carbonyl | 1-methylpiperidin-4-yl | benzyl | pyridin-4-ylmethyl | H |

TABLE-continued

| No. | ![structure](B with R1,R2,C,O) | ~(CH2)x—A | R5 | R3 | R4 |
|---|---|---|---|---|---|
| 27 | 2-methylpyridine-3-carbonyl | piperazine-N-methyl, N-R5 | 3-ethylphenyl-N(methyl)(benzyl) | benzyl (CH2CH2-Ph) | H |
| 28 | 2-methylpyridine-3-carbonyl | piperazine-N-methyl, N-R5 | 3-ethylphenyl-N(methyl)(benzyl) | benzyl | H |
| 29 | 2-methylpyridine-3-carbonyl | piperazine-N-ethyl, N-R5 | 3-ethyl-4-methylphenyl | benzyl | CONH2 |
| 30 | 2-methylpyridine-3-carbonyl | piperazine-N-ethyl, N-R5 | 4-ethyl-phenyl-one | benzyl | CONH2 |

TABLE-continued

| No. | -) | (CH2)x—A | R5 | R3 | R4 |
|---|---|---|---|---|---|
| 31 | 2-methylpyridine-3-carbonyl | piperidine-N-R5, with ethyl | 4-ethyl-N,N-dimethylaniline | benzyl (CH2-Ph) | CONH2 |
| 32 | 2-methylpyridine-3-carbonyl | piperidine-N-R5, with ethyl | 4-ethylphenyl | benzyl | CONH2 |
| 33 | 2-methylpyridine-3-carbonyl | piperidine-N-R5 | 4-ethyl-2-methyl-N-phenylaniline | benzyl | H |
| 34 | 2-methylbenzoyl | piperidine-N-R | 4-ethylphenyl (one) | benzyl | H |
| 35 | 2-methylbenzoyl | piperidine-N-R5 | 2-ethylphenyl | benzyl | H |

TABLE-continued

| No. | ![structure with R1,R2,B,C] | (CH₂)ₓ—A | R⁵ | R³ | R⁴ |
|---|---|---|---|---|---|
| 36 | 3-pyridyl-CHO | piperazine-N-R⁵ / N-Me | 4-ethylphenyl-COOH | Bn | H |
| 37 | 3-pyridyl-CHO | piperazine-N-R⁵ / N-Me | 4-ethylphenyl-SMe | Bn | H |
| 38 | 3-pyridyl-CHO | piperazine-N-R⁵ / N-Me | 4-ethylbenzyl-NMe₂ | Bn | H |
| 39 | 3-pyridyl-CHO | piperazine-N-R⁵ / N-Me | 4-ethylphenyl-C(O)NMe₂ | Bn | H |
| 40 | pyrimidine-CHO | piperazine-N-R⁵ / N-Me | 4-ethylphenyl-COOH | Bn | H |

TABLE-continued

| No. | ![structure](B with R1,R2,C,O) | (CH2)x—A | R5 | R3 | R4 |
|---|---|---|---|---|---|
| 41 | pyrimidine-carbaldehyde | piperazine-N-R5, N-Me | 4-(SMe)-phenyl-ethyl | Bn | H |
| 42 | pyrimidine-carbaldehyde | piperazine-N-R5, N-Me | 4-(NMe2-CH2)-phenyl-ethyl | Bn | H |
| 43 | pyrimidine-carbaldehyde | piperazine-N-R5, N-Me | 4-(OMe)-phenyl-ethyl | Bn | H |
| 44 | pyridine-carbaldehyde (methyl) | piperazine-N-R5, N-Me | 3-methyl-phenyl-ethyl | Bn | H |

TABLE-continued
| No. | | (CH₂)ₓ—A | R⁵ | R³ | R⁴ |
|---|---|---|---|---|---|
| 45 | 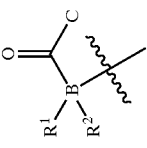 |  | 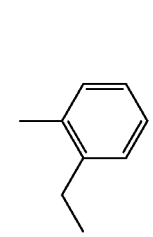 | Bn | H |
| 46 |  | 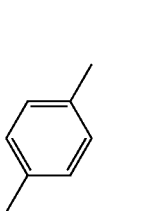 |  | Bn | H |
| 47 | 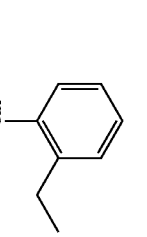 |  | 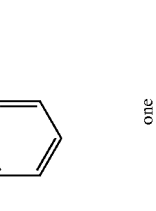 | Bn | H |
| 48 |  | 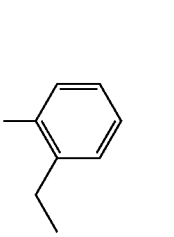 | | Bn | H |
| 49 | | | | Bn | H |

US 6,562,827 B1

TABLE-continued

| No. | ![structure with R1, R2, B, C and O] | (CH2)x—A | R5 | R3 | R4 |
|---|---|---|---|---|---|
| 50 | 4-methylpyridine-3-carbonyl | piperazine with N-Me and R5 | 3-ethylphenyl (one) | Bn | H |
| 51 | 4-methylpyridine-3-carbonyl | piperazine with N-Me and R5 | 4-ethylphenyl (one) | Bn | H |
| 52 | 4-methylpyridine-3-carbonyl | piperazine with N-Me and R5 | 4-ethylphenyl | Bn | H |
| 53 | 2-pyridinecarbonyl | piperazine N-R5 | 4-ethyl-2-OEt-phenyl | CH2-phenyl | CONH2 |
| 54 | 2-pyridinecarbonyl | piperazine N-R5 | 2-(N,N-diethylamino)phenyl with ethyl | CH2-phenyl | CONH2 |

| No. | $\underset{R^1 \; R^2}{\overset{O}{\underset{\|}{C}}\!\!-\!\!\overset{C}{\underset{\|}{B}}\!\!-}$ | $-(CH_2)_x\!-\!A$ | $R^5$ | $R^3$ | $R^4$ |
|---|---|---|---|---|---|
| 55 |  |  |  |  | H |
| 56 |  |  |  |  | CONH$_2$ |
| 57 |  |  |  |  | H |
| 58 |  |  |  |  | H |

TABLE-continued

| No. | (R1)(R2)) | (CH₂)ₓ—A | R⁵ | R³ | R⁴ |
|---|---|---|---|---|---|
| 59 | pyridinyl-carbonyl | piperidine N,N' with R⁵ | 3-aminophenylethyl | benzyl | CONH₂ |
| 60 | pyridine-carbaldehyde | piperazine-N-methyl-N'-R⁵ | 2-methylphenylethyl | benzyl | H |
| 61 | 2-methyl-5-nitrobenzaldehyde | piperazine-N-methyl-N'-R⁵ | 4-methoxyphenylethyl | benzyl | H |
| 62 | 2-methyl-5-nitrobenzaldehyde | piperazine-N-methyl-N'-R⁵ | 4-methylphenylethyl | benzyl | H |
| 63 | 2-methylbenzoyl | piperazine-N-ethyl-N'-R | 4-methoxyphenylethyl | butyl | H |

TABLE-continued

| No. | -) | (CH₂)ₓ—A | R⁵ | R³ | R⁴ |
|---|---|---|---|---|---|
| 64 | 2-methylbenzoyl | 4-ethyl-piperazin-1-yl | 4-methylphenyl | pentyl | H |
| 65 | 3-methylpyrazine-2-carbonyl | 4-R⁵-1-methylpiperazin-1-yl | phenyl | benzyl | H |
| 66 | 3-methylpyrazine-2-carbonyl | 4-R⁵-1-methylpiperazin-1-yl | 3-methylphenyl | benzyl | H |
| 67 | 3-methylpyridine-2-carbonyl | 4-R⁵-1-methylpiperidin-4-yl | phenyl | benzyl | H |
| 68 | 3-methylpyridine-2-carbonyl | 4-R⁵-1-methylpiperidin-4-yl | phenyl | pentyl | H |

TABLE-continued
| No. |  | (CH₂)ₓ—A | R⁵ | R³ | R⁴ |
|---|---|---|---|---|---|
| 69 | 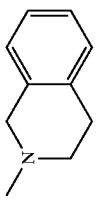 | 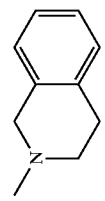 | H | 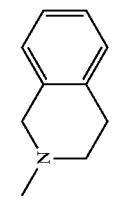 | H |
| 70 | 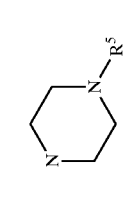 | 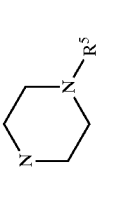 | H | 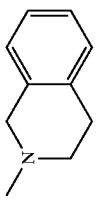 | CONH² |
| 71 | 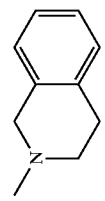 | 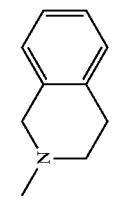 | H | 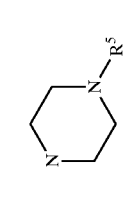 | CONH² |
| 72 | 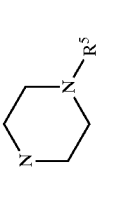 | 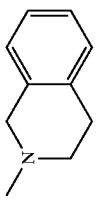 | 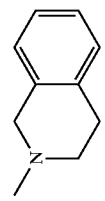 | 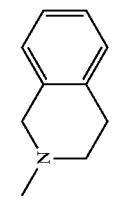 | H |
| 73 | 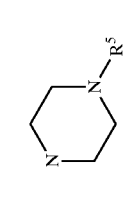 | 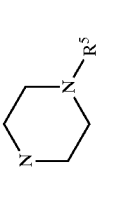 | 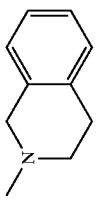 | 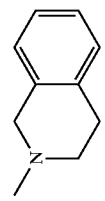 | H |

TABLE-continued

| No. | $\begin{array}{c}O\\\|\\C\\R^1\ B\ R^2\end{array}$ — (CH$_2$)$_x$—A | | R$^5$ | R$^3$ | R$^4$ |
|---|---|---|---|---|---|
| 74 | pyridine-CHO | morpholine-N-R$^5$ | 2,6-dichlorophenyl-ethyl | benzyl | H |
| 75 | pyridine-CHO | 4-methylpiperazine-N-R$^5$ | 2-Cl,6-OMe,ethyl,Cl-phenyl | benzyl | H |
| 76 | pyridine-CHO | 4-methylpiperazine-N-R$^5$ | 2-Cl,6-OMe,ethyl,Cl-phenyl | cyclohexylmethyl | H |
| 77 | pyridine-CHO | 4-methylpiperazine-N-R$^5$ | 2-Cl,6-OMe,ethyl,Cl-phenyl | 4-hydroxybenzyl | H |

TABLE-continued

| No. | ![structure with R1, R2, B, C, O] | –(CH₂)ₓ–A | R⁵ | R³ | R⁴ |
|---|---|---|---|---|---|
| 78 | 2-acyl-Z-phenyl | 1-ethyl-3-R⁵-piperidinyl | benzyl | benzyl | H |
| 79 | 2-acyl-Z-phenyl | 1-ethyl-3-R⁵-piperidinyl | 3-methylbenzyl | benzyl | H |
| 80 | 2-acyl-Z-phenyl | 1-ethyl-4-R⁵-piperidinyl | benzyl | benzyl | H |
| 81 | 2-acyl-Z-phenyl | 1-ethyl-4-R⁵-piperidinyl | 3-methylbenzyl | benzyl | H |

TABLE-continued

| No. | (R2)-B-C) | (CH2)x—A | R5 | R3 | R4 |
|---|---|---|---|---|---|
| 82 | 2-acyl-4,5-dimethoxypyridine | piperazine-N-R5 | benzyl | benzyl | H |
| 83 | 2-acyl-4,5-dimethoxypyridine | piperazine-N-R5 | benzyl | isobutyl | H |
| 84 | 2-acyl-4-methoxyphenyl | piperazine-N-R5 | benzyl | benzyl | H |
| 85 | 2-acyl-4-methoxyphenyl | piperazine-N-R5 | benzyl | cyclohexyl | H |
| 86 | 2-acyl-5-methylphenyl | piperazine-N-R5 | methylphenyl | benzyl | H |

TABLE-continued
| No. | 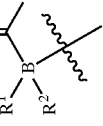 | (CH$_2$)$_x$—A | R$^5$ | R$^3$ | R$^4$ |
|---|---|---|---|---|---|
| 87 | 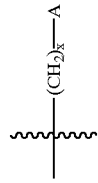 |  |  |  | CONH$_2$ |
| 88 | 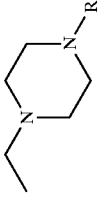 | 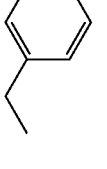 |  |  | H |
| 89 | 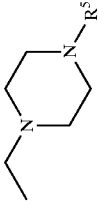 | 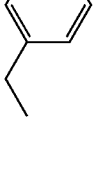 |  |  | CONH$_2$ |
| 90 | 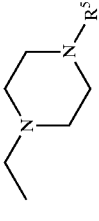 | 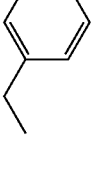 |  |  | H |

TABLE-continued

| No. | with R1, R2, B, C; pyridine-carbonyl) | (CH₂)ₓ—A | R⁵ | R³ | R⁴ |
|---|---|---|---|---|---|
| 91 | 3-pyridyl carbonyl | piperazine-N-R⁵, N-Me | 4-ethylphenyl (OMe) | Bn | CONH₂ |
| 92 | 3-pyridyl carbonyl | piperazine-N-R⁵, N-Me | 2-ethyl-6-methylphenyl | Bn | CONH₂ |
| 93 | 3-pyridyl carbonyl | piperazine-N-R⁵, N-Me | 4-ethylphenyl | Bn | CONH₂ |
| 94 | 3-pyridyl carbonyl | piperazine-N-R⁵, N-Me | 2-ethylphenyl (OMe) | Bn | CONH₂ |

TABLE-continued

| No. | $\begin{array}{c}O\\\|\\R^1-C-C\\R^2\end{array}$ | $-(CH_2)_x-A$ | $R^5$ | $R^3$ | $R^4$ |
|---|---|---|---|---|---|
| 95 | pyridinyl-C(O)- | N-methylpiperazinyl-$R^5$ | 3-ethylphenyl | Bn | $CONH_2$ |
| 96 | pyridinyl-C(O)- | N-methylpiperazinyl-$R^5$ | 3-ethylphenyl | Bn | $CONH_2$ |
| 97 | pyridinyl-C(O)- | N-methylpiperazinyl-$R^5$ | 2-ethyl-(one)phenyl | Bn | $CONH_2$ |
| 98 | pyridinyl-C(O)- | N-methylpiperazinyl-$R^5$ | 3-ethyl-(one)phenyl | Bn | $CONH_2$ |

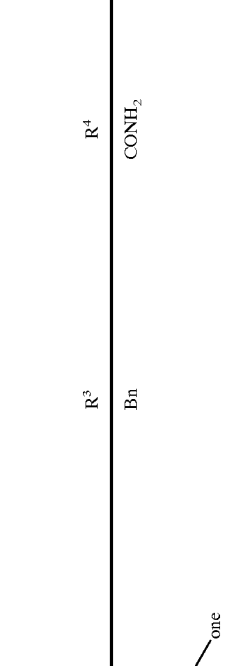

TABLE-continued

| No. | -B(R¹)(R²)-C) | (CH₂)ₓ—A | R⁵ | R³ | R⁴ |
|---|---|---|---|---|---|
| 103 | 3-formylpyridin-4-yl | piperazin-N-R⁵ | 4-nitrophenyl-ethyl | pentyl | H |
| 104 | 3-formylpyridin-4-yl | piperazin-N-R⁵ | 2-nitrophenyl-ethyl | pentyl | H |
| 105 | 3-formylpyridin-4-yl | piperazin-N-R⁵ | benzo[1,3]dioxol-5-yl-ethyl | benzyl | CONH₂ |
| 106 | 3-formylpyridin-4-yl | piperazin-N-R⁵ | benzo[1,3]dioxol-5-yl-ethyl | butyl | H |

TABLE-continued

| No. | (structure) | (CH₂)ₓ—A | R⁵ | R³ | R⁴ |
|---|---|---|---|---|---|
| 107 | 3-pyridyl carbonyl | piperazinyl-R⁵ | benzo[1,3]dioxol-5-ylethyl | pentyl | CONH₂ |
| 108 | 3-pyridyl carbonyl | piperazinyl-R⁵ | 4-(methoxy)phenylethyl | 4-hydroxyphenylethyl | CONH₂ |
| 109 | 3-pyridyl carbonyl | piperazinyl-R⁵ | 4-(ethoxy)phenylethyl | 4-hydroxyphenylethyl | CONH₂ |
| 110 | 3-pyridyl carbonyl | piperazinyl-R⁵ | 4-(benzyloxy)phenylethyl | cyclohexylethyl | CONH₂ |

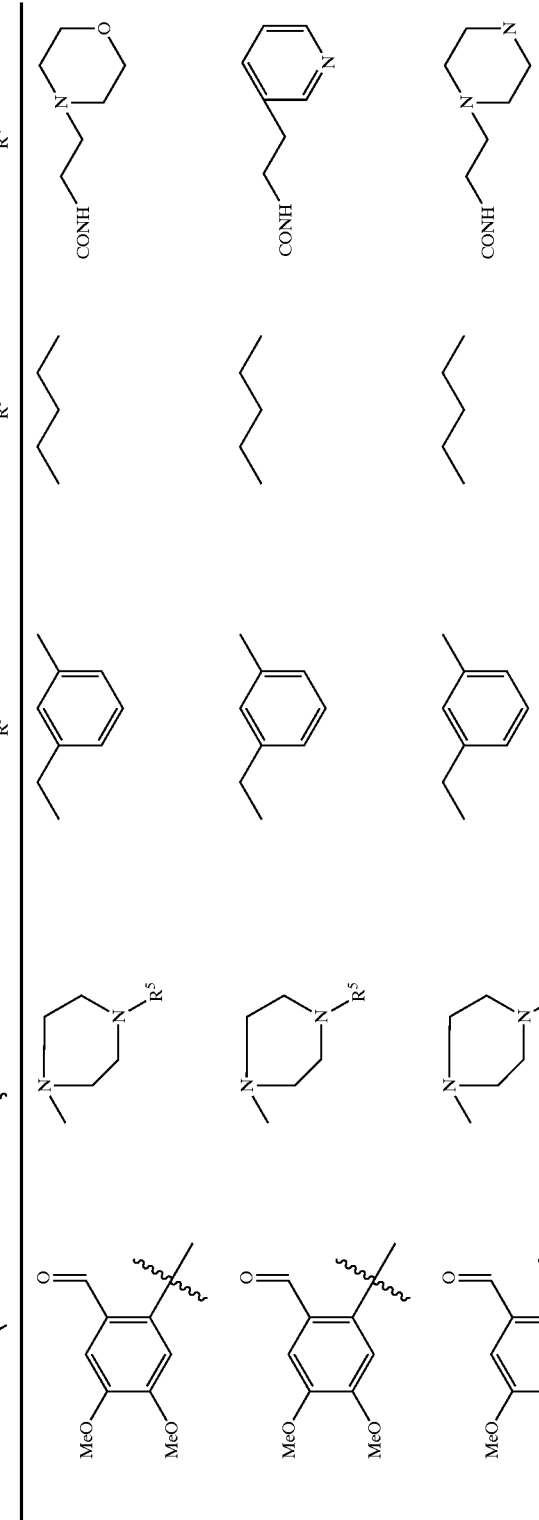

TABLE-continued

| No. | ![structure] | (CH₂)ₓ—A | R⁵ | R³ | R⁴ |
|---|---|---|---|---|---|
| 115 | 2-CHO-5-NO₂-phenyl | piperazine-N-Me / N-R⁵ | 3-ethylphenyl | pentyl | CONH-CH₂CH₂-morpholine |
| 116 | 2-CHO-5-NO₂-phenyl | piperazine-N-Me / N-R⁵ | 3-ethylphenyl (one) | 4-ethylphenol | CONH₂ |
| 117 | 2-CHO-5-NO₂-phenyl | piperazine-N-Me / N-R⁵ | 4-ethyl-NO₂-phenyl | ethylcyclohexyl | CONH₂ |
| 118 | 2-CHO-5-NO₂-phenyl | piperazine-N-Me / N-R⁵ | 4-ethyl-OEt-phenyl | ethylcyclohexyl | CONH₂ |

TABLE-continued

| No. | $\underset{R^2}{\overset{O}{\underset{R^1}{\|}}}\overset{C}{\underset{B}{\sim}}$ | (CH$_2$)$_x$—A | R$^5$ | R$^3$ | R$^4$ |
|---|---|---|---|---|---|
| 119 | 2-CHO, 5-O$_2$N-phenyl | homopiperazinyl-N-R$^5$ (N-methyl) | 4-ethylphenyl (one) | cyclohexylmethyl | 2-(pyridin-3-yl)ethyl-CONH |
| 120 | 2-CHO, 5-O$_2$N-phenyl | homopiperazinyl-N-R$^5$ (N-methyl) | 4-ethylphenyl | cyclohexylmethyl | 2-(pyridin-3-yl)ethyl-CONH |
| 121 | 3-CHO-pyridin-4-yl | piperazinyl-N-R$^5$ | 3-methylbenzyl | benzyl | H |
| 122 | 3-CHO-pyridin-4-yl | piperazinyl-N-R$^5$ | 4-methylbenzyl | benzyl | H |

TABLE-continued

| No. | $\begin{array}{c}O\\\parallel\\C\\/\ \backslash\\R^1\ R^2\end{array}$ B—C | (CH$_2$)$_x$—A | R$^5$ | R$^3$ | R$^4$ |
|---|---|---|---|---|---|
| 123 | 3-formyl-pyridin-4-yl | morpholin-N-yl with N-R$^5$ | 4-(dimethylaminomethyl)benzyl | benzyl | H |
| 124 | 3-formyl-pyridin-4-yl | morpholin-N-yl with N-R$^5$ | 2-(dimethylaminomethyl)benzyl | benzyl | H |
| 125 | 3-formyl-pyridin-4-yl | morpholin-N-yl with N-R$^5$ | 2-(dimethylamino)benzyl | benzyl | H |
| 126 | 3-formyl-pyridin-4-yl | morpholin-N-yl with N-R$^5$ | 2-(dimethylamino)benzyl | benzyl | H |

TABLE-continued

| No. | -) | (CH2)x—A | R5 | R3 | R4 |
|---|---|---|---|---|---|
| 127 | 3-formyl-pyridin-4-yl | piperazinyl-N-R5 | 3-ethyl-phenyl (methyl) | benzyl | H |
| 128 | 3-formyl-pyridin-4-yl | piperazinyl-N-R5 | 3-ethyl-phenyl (methyl) | benzyl | CONH2 |
| 129 | 3-formyl-pyridin-4-yl | piperazinyl-N-R5 | 3-ethyl-phenyl (one) | benzyl | H |
| 130 | 3-formyl-pyridin-4-yl | piperazinyl-N-R5 | ethyl-benzo[1,3]dioxol-yl | benzyl | H |

TABLE-continued

| No. | | -(CH2)x-A | R5 | R3 | R4 |
|---|---|---|---|---|---|
| 131 | 3-formylpyridin-4-yl | morpholine N-R5 | 6-ethylnaphthalen-2-yl | pentyl | CONH2 |
| 132 | 3-formylpyridin-4-yl | morpholine N-R5 | 6-ethylnaphthalen-2-yl | benzyl | CONH2 |
| 133 | 2-formyl-4-nitrophenyl | 4-ethylpiperazine N-R5 | 6-ethylnaphthalen-2-yl | benzyl | CONH2 |
| 134 | 2-formyl-4-nitrophenyl | 4-ethylpiperazine N-R5 | 6-ethylnaphthalen-2-yl | pentyl | CONH2 |

TABLE-continued

| No. | $\begin{array}{c}O\\\parallel\\R^1-C-B-C\\R^2\end{array}$ | —(CH$_2$)$_x$—A | R$^5$ | R$^3$ | R$^4$ |
|---|---|---|---|---|---|
| 135 | 2-CHO, 4-O$_2$N-phenyl | piperazinyl-N-R$^5$ | ethyl-naphthyl | ethyl-cyclohexyl | CONH$_2$ |
| 136 | 2-CHO, 4-O$_2$N-phenyl | piperazinyl-N-R$^5$ | ethyl-naphthyl | ethyl-cyclohexyl | CONH$_2$ |
| 137 | 2-CHO, 4-O$_2$N-phenyl | piperazinyl-N-R$^5$ | ethyl-naphthyl | ethyl-phenyl | CONH$_2$ |
| 138 | 2-CHO, 4-MeO-phenyl | piperazinyl-N-R$^5$ | ethyl-naphthyl | ethyl-phenyl | CONH$_2$ |

TABLE-continued

| No. | (structure with R¹, R², B, C) | (CH₂)ₓ—A | R⁵ | R³ | R⁴ |
|---|---|---|---|---|---|
| 139 | 2-formyl-5-methoxyphenyl | 4-ethylpiperazin-1-yl (N-R⁵) | 6-ethylnaphthalen-2-yl | pentyl | CONH₂ |
| 140 | 3-oxo-pyridin-4-yl | 2-methyl-1,2,3,4-tetrahydroisoquinolin-6-yl (R⁵) | H | propyl | H |
| 141 | 3-oxo-pyridin-4-yl | 2-methyl-1,2,3,4-tetrahydroisoquinolin-6-yl (R⁵) | H | butyl | H |
| 142 | 3-oxo-pyridin-4-yl | 2-methyl-1,2,3,4-tetrahydroisoquinolin-6-yl (R⁵) | H | butyl | CONH₂ |
| 143 | 3-oxo-pyridin-4-yl | 2-methyl-1,2,3,4-tetrahydroisoquinolin-6-yl (R⁵) | H | butyl | CONH₂ |

TABLE-continued
| No. | | (CH₂)ₓ—A | R⁵ | R³ | R⁴ |
|---|---|---|---|---|---|
| 144 | 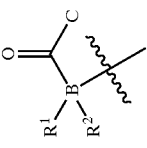 | 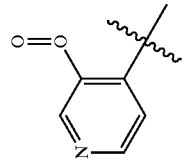 | 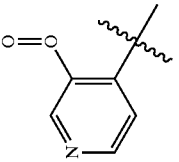 | 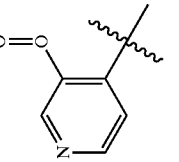 | CONH₂ |
| 145 | 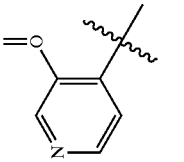 | 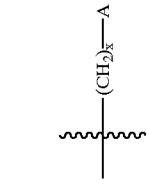 | 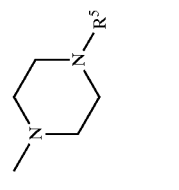 | 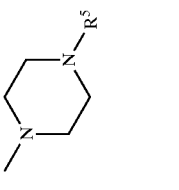 | CONH₂ |
| 146 | 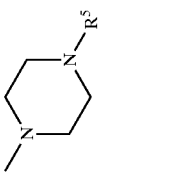 | 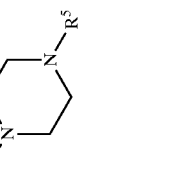 | 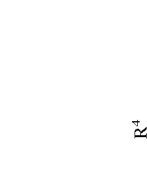 |  | CONH₂ |
| 147 |  |  |  |  | CONH₂ |

TABLE-continued

| No. | C(=O)—) | —(CH₂)ₓ—A | R⁵ | R³ | R⁴ |
|---|---|---|---|---|---|
| 148 | 2-CHO-5-MeO-phenyl | piperazine-N-R⁵ with N-ethyl | benzyl | 4-pyridylmethyl | H |
| 149 | 2-CHO-5-MeO-phenyl | piperazine-N-R⁵ with N-ethyl | benzyl | 4-pyridylmethyl | CONH₂ |
| 150 | 2-CHO-5-MeO-phenyl | piperazine-N-R⁵ with N-ethyl | benzyl | 4-pyridylmethyl | morpholinoethyl-CONH |
| 151 | 2-CHO-4,5-diMeO-phenyl | homopiperazine-N-R⁵ with N-ethyl | 3-methylbenzyl | isobutyl | H |

TABLE-continued

| No. | ![structure] | (CH₂)ₓ—A | R⁵ | R³ | R⁴ |
|---|---|---|---|---|---|
| 152 | 2,4-di-MeO-benzoyl | piperazine-N-R⁵ with N-ethyl | 4-ethylphenyl | pentyl | H |
| 153 | 2,4-di-MeO-benzoyl | piperazine-N-R⁵ with N-ethyl | 2-ethylphenyl | pentyl | H |
| 154 | 2,4-di-MeO-benzoyl | piperazine-N-R⁵ with N-ethyl | 6-ethyl-2-naphthyl | butyl | H |
| 155 | 2-CHO-4-O₂N-benzoyl | piperazine-N-R⁵ with N-ethyl | 3-ethylphenyl | butyl | H |

TABLE-continued

| No. | ![structure with R1, R2, B, C] | (CH2)x—A | R5 | R3 | R4 |
|---|---|---|---|---|---|
| 156 | 2-CHO, 4-NO2-phenyl | piperazine-N-R5 | 3-ethylphenyl (one) | pentyl | H |
| 157 | 2-CHO, 4-NO2-phenyl | piperazine-N-R5 | 4-ethylphenyl | 4-hydroxyphenyl | H |
| 158 | 2-CHO, 4-NO2-phenyl | piperazine-N-R5 | 4-ethyl-nitrophenyl | cyclohexylmethyl | H |
| 159 | 2-CHO, 4-NO2-phenyl | piperazine-N-R5 | 4-ethyl-OEt-phenyl | cyclohexylmethyl | H |

TABLE-continued

| No. | $\begin{array}{c}O\\\parallel\\R^1-C-B\\R^2\end{array}$ C | —(CH$_2$)$_x$—A | R$^5$ | R$^3$ | R$^4$ |
|---|---|---|---|---|---|
| 160 | 3-formylpyridin-4-yl | piperazinyl-N-R$^5$ | 6-ethylnaphthalen-2-yl | pentyl | H |
| 161 | 3-formylpyridin-4-yl | piperazinyl-N-R$^5$ | 6-ethylnaphthalen-2-yl | benzyl | H |
| 162 | 2-formyl-4-nitrophenyl | 4-ethylpiperazin-1-yl-N-R$^5$ | 6-ethylnaphthalen-2-yl | benzyl | H |
| 163 | 2-formyl-4-nitrophenyl | 4-ethylpiperazin-1-yl-N-R$^5$ | 6-ethylnaphthalen-2-yl | pentyl | H |

TABLE-continued

| No. | $\begin{array}{c}O\\\parallel\\R^1-C\\R^2\end{array}$ B—C | —(CH$_2$)$_x$—A | R$^5$ | R$^3$ | R$^4$ |
|---|---|---|---|---|---|
| 164 | 2-CHO-4-O$_2$N-phenyl | piperazinyl-N-R$^5$ (ethyl) | ethyl-naphthyl | ethyl-cyclohexyl | H |
| 165 | 2-CHO-5-O$_2$N-phenyl | piperazinyl-N-R$^5$ (ethyl) | ethyl-naphthyl | ethyl-cyclohexyl | H |
| 166 | 2-CHO-5-O$_2$N-phenyl | piperazinyl-N-R$^5$ (ethyl) | ethyl-naphthyl | ethyl-phenyl | H |
| 167 | 2-CHO-4-MeO-phenyl | piperazinyl-N-R$^5$ (ethyl) | ethyl-naphthyl | ethyl-phenyl | H |

TABLE-continued

| No. | (R²)-B-C, wavy) | -(CH₂)ₓ-A | R⁵ | R³ | R⁴ |
|---|---|---|---|---|---|
| 168 | 2-MeO-benzaldehyde | piperazine-N-R⁵ with ethyl | 6-ethyl-naphthalen-2-yl | isopentyl | H |
| 169 | 2-formyl-pyridin-3-yl | piperazine-N-R⁵ with ethyl | 3-ethyl-4-methyl-phenyl | benzyl | 2-(pyridin-2-yl)ethyl-CONH |
| 170 | 2-formyl-pyridin-3-yl | piperazine-N-R⁵ with ethyl | 3-ethyl-4-methyl-phenyl | benzyl | 2-(2H-pyran-3-yl)ethyl-CONH |
| 171 | 2-formyl-pyridin-3-yl | piperazine-N-R⁵ with ethyl | 6-ethyl-naphthalen-2-yl | benzyl | 2-(pyridin-2-yl)ethyl-CONH |

TABLE-continued

| No. | ![structure](B with R¹, R² and C attached, with C=O) | ⟨(CH₂)ₓ—A⟩ | R⁵ | R³ | R⁴ |
|---|---|---|---|---|---|
| 172 | pyridine-2,3-dicarbaldehyde linker | piperazine-N-ethyl, N-R⁵ | naphthyl-ethyl | benzyl | pyridinium-ethyl-CONH |
| 173 | pyridine-2,3-dicarbaldehyde linker | diazepane-N-ethyl, N-R⁵ | 4-methoxyphenyl-ethyl | pentyl | pyridinium-ethyl-CONH |
| 174 | pyridine-2,3-dicarbaldehyde linker | diazepane-N-ethyl, N-R⁵ | 4-ethoxyphenyl-ethyl | pentyl | pyridinium-ethyl-CONH |
| 175 | pyridine-2,3-dicarbaldehyde linker | diazepane-N-ethyl, N-R⁵ | 4-ethoxyphenyl-ethyl | benzyl | pyridinium-ethyl-CONH |

TABLE-continued

| No. | | (CH2)x—A | R5 | R3 | R4 |
|---|---|---|---|---|---|
| 176 | pyridine-2,3-diyl with C=O | piperazine-N-R5 with ethyl | 4-ethylphenyl-one | benzyl (phenyl-CH2) | CONH-CH2CH2-(oxazine N) |
| 177 | pyridine-2,3-diyl with C=O | piperazine-N-R5 with ethyl | 4-ethylphenyl-one | benzyl | CONH-CH2CH2-(2-pyridyl) |
| 178 | 4-CO-pyridine | piperazine-N-R5 with ethyl | Bu | Bu | CONH-CH2CH2-(2-pyridyl) |
| 179 | pyridine-2,3-diyl with C=O | piperazine-N-R5 | 4-ethylphenyl-COOU | Bn | CONH2 |

TABLE-continued

| No. | (R2)-C) | (CH2)x—A | R5 | R3 | R4 |
|---|---|---|---|---|---|
| 180 | 3-formyl-2-pyridyl | piperazinyl-R5 | 4-ethylphenyl-SMe | Bn | CONH2 |
| 181 | 3-formyl-2-pyridyl | piperazinyl-R5 | 4-ethylphenyl-NMe2 | Bn | CONH2 |
| 182 | 3-formyl-2-pyridyl | piperazinyl-R5 | 4-ethylphenyl-C(=CH2)NMe2 | Bn | CONH2 |
| 183 | 3-formyl-2-pyridyl | piperazinyl | 4-ethylphenyl-NMe2 | Bn | H |

TABLE-continued

| No. | $\underset{R^1\ R^2}{\overset{O}{\underset{\|}{C}}}\overset{C}{\underset{B}{\sim}}$ | –(CH$_2$)$_x$–A | R$^5$ | R$^3$ | R$^4$ |
|---|---|---|---|---|---|
| 184 | 3-formyl-2-pyridyl | piperazinyl-N-R$^5$ | 3-ethylphenyl | Bn | CONH$_2$ |
| 185 | 3-formyl-2-pyridyl | piperazinyl-N-R$^5$ | 6-ethyl-2-naphthyl | Bn | CONH$_2$ |
| 186 | 3-formyl-2-pyridyl | piperazinyl-N-R$^5$ | (2-ethyl-3-pyridyl)methyl-N(Et)$_2$ | Bn | CONH$_2$ |
| 187 | 3-formyl-4-pyridyl | piperazinyl-N-R$^5$ | (4-ethylphenyl)methyl-N(Me)$_2$ | Bn | CONH$_2$ |

We claim:
1. A compound of formula I

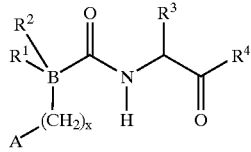

or a tautomeric or isomeric form, an enantiomeric or diastereomeric form, or a physiologically tolerable salt, wherein A is piperazine, homopiperazine, hexahydroazepine, piperidine or pyrrolidine, which can additionally carry a radical $R^5$ and B is a phenyl, pyridine, pyrimidine, pyrazine or pyridazine ring and $R^1$ and $R^2$ independently of one another are hydrogen, $C_1$–$C_6$-alkyl, which is branched or unbranched, O—$C_1$–$C_6$-alkyl, which is branched or unbranched, OH, Cl, F, Br, I, $CF_3$, $NO_2$, $NH_2$, CN, COOH, COO—$C_1$–$C_4$-alkyl, NHCO—$C_1$–$C_4$-alkyl, NHCO-phenyl, CONHR$^9$, NHSO$_2$—$C_1$–$C_4$-alkyl, NHSO$_2$-phenyl, SO$_2$—$C_1$–$C_4$-alkyl and SO$_2$-phenyl and $R^1$ and $R^2$ can be a chain —CH═CH—CH═CH—, which can additionally carry one or two substituents $R^6$, and $R^3$ is $C_1$–$C_6$-alkyl, which is branched or unbranched and which can additionally carry an S—$CH_3$ radical, cyclohexyl, cyclopentyl, cycloheptyl, phenyl, pyridyl, pyrimidyl, pyridazyl, pyrazinyl, indolyl, thienyl or naphthyl ring, where the rings are substituted by at most two radicals $R^7$ and $R^7$ is hydrogen, $C_1$–$C_4$-alkyl, which is branched or unbranched, O—$C_1$–$C_4$-alkyl, OH, Cl, F, Br, I, $CF_3$, $NO_2$, $NH_2$, CN, COOH, COO—$C_1$–$C_4$-alkyl, CONHR$^9$, NHCO—$C_1$–$C_4$-alkyl, NHCO-phenyl, NHSO$_2$—$C_1$–$C_4$-alkyl, NHSO$_2$-phenyl, SO$_2$—$C_1$–$C_4$-alkyl and SO$_2$-phenyl, and $R^4$ is hydrogen, —COR$^8$, where $R^8$ can be —OR$^9$ and —NR$^9$R$^{10}$ and $R^5$ is hydrogen, $C_1$–$C_6$-alkyl, which is branched or unbranched, which can additionally carry a substituent $R^{11}$, or $R^5$ can be a phenyl, pyridyl, pyrimidyl, pyridazyl, pyrazinyl, pyrazyl, naphtyl, thienyl, piperidinyl, pyrrolidinyl or imidazolyl ring, which can additionally carry one or two substituents $R^6$ and $R^6$ is hydrogen, $C_1$–$C_6$-alkyl, which is branched or unbranched, O—$C_1$–$C_6$-alkyl, which is branched or unbranched, OH, Cl, F, Br, I, $CF_3$, $NO_2$, $NH_2$, CN, COOH, COO—$C_1$–$C_4$-alkyl or $C_1$–$C_4$-alkyl-NR$^9$R$^{13}$ or two radicals $R^6$ can be a bridge OC(R$^9$)$_2$O and $R^9$ is hydrogen, $C_1$–$C_6$-alkyl, which is branched or unbranched, and $R^{10}$ is hydrogen, $C_1$–$C_6$-alkyl, which is branched or unbranched, which can additionally be substituted by a phenyl ring which can additionally carry a radical $R^{12}$, and by

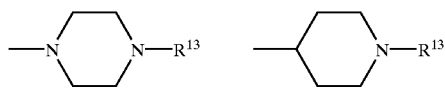

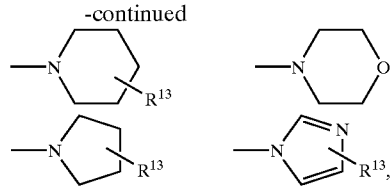

and $R^{11}$ can be a phenyl, pyridyl, pyrimidyl, naphtyl, thienyl, furyl, pyridazyl, pyrazinyl, pyrazolyl, pyrrolyl or imidazolyl ring which can additionally carry one or two substituents $R^6$, and $R^{12}$ is hydrogen, $C_1$–$C_6$-alkyl, which is branched or unbranched, O—$C_1$–$C_6$-alkyl, which is branched or unbranched, OH, Cl, F, Br, I, $CF_3$, $NO_2$, $NH_2$, CN, COOH, COO—$C_1$–$C_4$-alkyl and $R^{13}$ is hydrogen, a $C_1$–$C_4$-alkyl chain and $C_0$–$C_4$-alkylphenyl, where the phenyl ring can additionally carry one or two radicals $R^{12}$ and x is 0, 1 or 2.

2. The compound of formula I defined in claim 1, where $R^4$ is hydrogen.

3. The compound of formula I defined in claim 1, where $R^4$ is CONR$^9$R$^{10}$.

4. The compound of formula I defined in claim 1, where B is pyridine or phenyl and $R^4$ is hydrogen.

5. The compound of formula I defined in claim 1, where B is pyridine or phenyl and $R^4$ is CONR$^9$R$^{10}$.

6. The compound of formula I defined in claim 1, where A is piperazine and B is pyridine or phenyl and $R^4$ is hydrogen.

7. The compound of formula I defined in claim 1, where A is piperazine and B is pyridine or phenyl and $R^4$ is CONR$^9$R$^{10}$.

8. The compound of formula I defined in claim 1, where A is piperazine and B is ortho-substituted pyridine or phenyl and $R^4$ is hydrogen.

9. The compound of formula I defined in claim 1, where A is piperazine and B is ortho-substituted pyridine or phenyl and $R^4$ is CONR$^9$R$^{10}$.

10. The compound of formula I defined in claim 1, wherein the group A—(CH$_2$)$_x$ and the group C(═O)—NH—CHR$^3$—C(═O)—R$^4$ are bonded to adjacent members of the ring represented by B.

11. A pharmaceutical preparation comprising an effective amount of the compound of formula I defined in claim 1 and at least one customary pharmaceutical auxiliary.

12. A pharmaceutical preparation for oral, parenteral and intraperitoneal use, comprising per individual dose, in addition to the customary pharmaceutical auxiliaries, at least one compound of formula I defined in claim 1.

13. A method for the treatment of diseases in which increased calpain activity occurs comprising administering an effective amount of the preparation defined in claim 11.

14. A method for the treatment of neurodegenerative diseases and neuronal damage comprising administering an effective amount of the preparation defined in claim 11.

15. The method defined in claim 14, wherein the neurodegenerative diseases or neuronal damage are caused by ischemia, trauma or mass hemorrhages.

16. The method defined in claim 14 for the treatment of cerebral stroke and craniocerebral trauma.

17. The method defined in claim 14 for the treatment of Alzheimer's disease and Huntington's disease.

18. A method for the treatment of damage to the heart after cardiac ischemias, damage and reperfusion after vascular occlusion, damage to the kidneys after renal ischemias, skeletal muscular damage, muscular dystrophies, damage which results due to proliferation of the smooth muscle cells, coronary vasospasm, cerebral vasospasm, cataracts of the eyes and restenosis of the bloodstreams after angioplasty which comprises administering an effective amount of the preparation defined in claim 11.

19. The method defined in claim 18 for the treatment of tumors and metastasis thereof.

20. The method defined in claim 18 for the treatment of diseases in which increased interleukin-1 levels occur.

21. The method defined in claim 18 for the treatment of inflammations and rheumatic disorders.

22. A method for the inhibition of cysteine proteases, comprising administering an effective amount of the preparation defined in claim 11.

23. The method defined in claim 22, wherein the cysteine proteases are calpains and cathepsins B and L.

* * * * *